United States Patent [19]
Petryshyn

[11] Patent Number: 6,124,091
[45] Date of Patent: Sep. 26, 2000

[54] CELL GROWTH-CONTROLLING OLIGONUCLEOTIDES

[75] Inventor: Raymond A. Petryshyn, Hume, Va.

[73] Assignee: Research Corporation Technologies, Inc., Tucson, Ariz.

[21] Appl. No.: 08/867,230

[22] Filed: May 30, 1997

[51] Int. Cl.$^7$ .............................. C07H 71/04; C12Q 1/68; C12N 15/85; A61K 48/00
[52] U.S. Cl. .......................... 435/6; 435/91.1; 435/320.1; 435/325; 435/375; 514/44; 536/23.1; 536/24.5
[58] Field of Search ............................... 435/6, 69.1, 183, 435/91.1, 320.1, 325, 375, 440; 514/44; 536/23.1, 24.3, 24.33, 24.5

[56] References Cited

PUBLICATIONS

Branch, TIBS: 45–50 (Feb. 1998).
R.K. Maitra, et al., (1995) "Catalytic cleavage of an RNA target by 2–5A antisense and RNase L", *J. Biol. Chem.*, 270 (25):15071–5.
E. Ohtsubo, et al., (1994) "Identification of the region that determines the specifity of binding of the tranposases encoded by Tn3 and gamma, delta to the terminal inverted repeat sequences", *Japanese J. Genetics*, 69:269–85.
R.A. Petryshyn et al. (1997) "Characterization and mapping of the double-standard regions involved in activation of PKR within a cellular RNA from 3T3–F442A cells", *Nucleic Aids Research*, 25 (13):2672–78.
R.A. Petryshyn, et al., (1991) "Activation of the double-standard RNA–dependent eIF–2–alpha kinase by cellular RNA from 3T3–F442A cells", *E. J. Biochem*, 195:41–8.
B.K. Thelma, (1996) JD=NITNREPSQ, AC=X96404, "Horizontal transfer of sequences identical to an internal fragment segment of bacterial transposon Tn1000 is widespread in the genome including humans", XP002078962.
Broom, et al. (1995) "Sequence of a transposon identified as Tn1000(γδ)", *DNA Sequence—The Journal of Sequencing and Mapping*, 5:185–189.
Chong, et al. (1992) "Human p68 kinase exhibits growth suppression in yeast and homology to the translation regulator GCN2", *EMBO Journal*, 11:1553–1562.
Jinhe, et al. (1991) "Activation of the double-stranded RNA–dependent EIF–2α kinase by cellular RNA from 3T3–F442A cells", *Eur. J. Biochem*, 195:41–48.
Judware, et al. (1992) "Mechanism of Action of a Cellular Inhibitor of the dsRNA–Dependent Protein Kinase from 3T3–F442A Cells", *The Journal of Biological Chemistry*, 267:21685–21690.
Judware, et al. (1993) "Inhibition of the dsRNA–Dependent Protein Kinase by a Peptide Derived from the Human Immunodeficiency Virus Type 1 Tat Protein", *Journal of Interferon Research*, 13:153–160.
Khan, et al. (1992) Single pass sequencing and physical and genetic mapping of human brain cSNAs, *nature genetics*, 2:180–185.
Maekawa, et al. (1994) "Identification of the region that determined the specificity of binding of the transposases encoded by Tn3 and γδ to the terminal inverted repeat sequences", *Jpn. J. Genet.*, 69:269–285.
Nekhai, et al. (1996) "Peptides Derived from the Interferon–Induced PKR Prevent Activation by HIV–1 TAR RNA", *Virology*, 221:000–000.
Petryshyn, et al. (1984) "Growth–related Expression of a Double–stranded RNA–dependent Protein Kinase in 3T3 Cells", *The Journal of Biological Chemistry*, 259:14736–14742.
Petryshyn, et al. (1988) "Detection of activated double–stranded RNA–dependent protein kinase in 3T3–F442A cells", *Proc. Natl. Acad. Sci. USA*, 85:1427–1431.
Petryshyn, et al. (1994) "Activation of the dsRNA–Dependent Kinase", *Progress in Molecular and subcellular Biology*, 14:1–14.
Petryshyn, et al. (1996) "Effect of Interferon on Protein Translation during Growth Stages of 3T3 Cells", *Archives of Biochemistry and Biophysics*, 328:290–297.
Li, J. and Petryshyn, R., GenBank Accession No. M93663, published Mar. 5, 1996.

*Primary Examiner*—George C. Elliott
*Assistant Examiner*—Andrew Wang
*Attorney, Agent, or Firm*—Scully, Scott, Murphy & Presser

[57] ABSTRACT

The present invention provides a partial cDNA corresponding to an RNA containing double stranded regions (R-RNA), which, when transcribed in vitro, gives rise to an RNA transcript that activates PKR. An approximately 226–252 bp nucleotide (nt) sequence responsible for activation of PKR (the activation sequence) has been identified within the cDNA and isolated. Antisense oligonucleotides corresponding to specific portions of the 252 nt cDNA fragment stimulate proliferation of different cells in culture. Various portions of the cDNA or R-RNA may also be used to inhibit cell proliferation in cell cultures.

The present invention further provides pharmaceutical compositions comprising the subject nucleic acid fragments and oligonucleotides. Kits which comprise at least one of the subject isolated nucleic acid molecules or oligonucleotides and a pharmaceutically acceptable carrier are also provided.

27 Claims, 18 Drawing Sheets

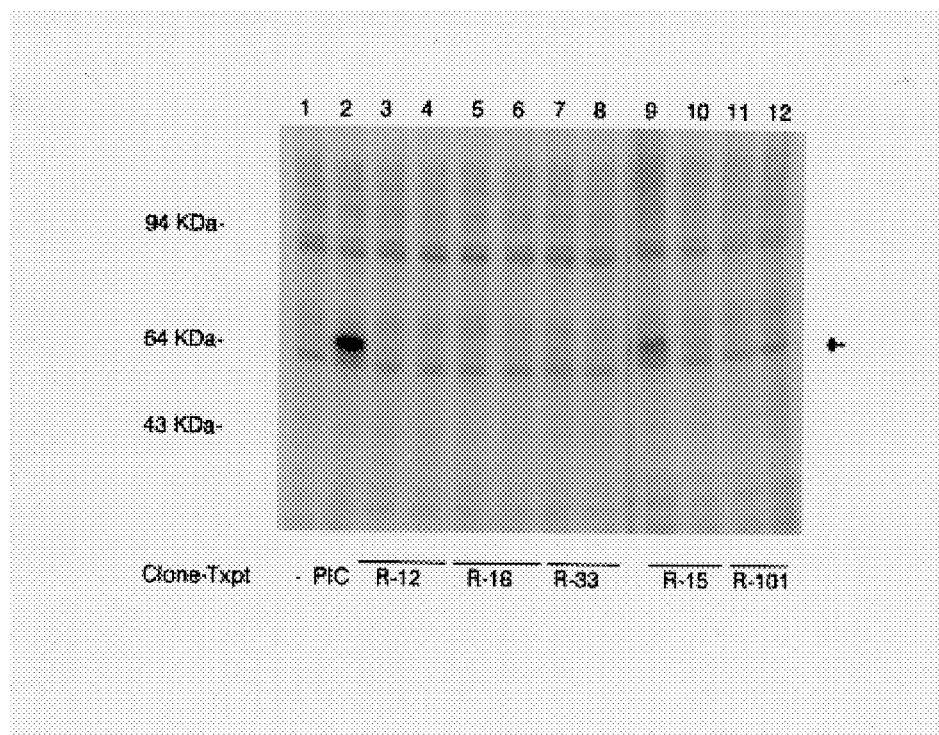
FIG. IA
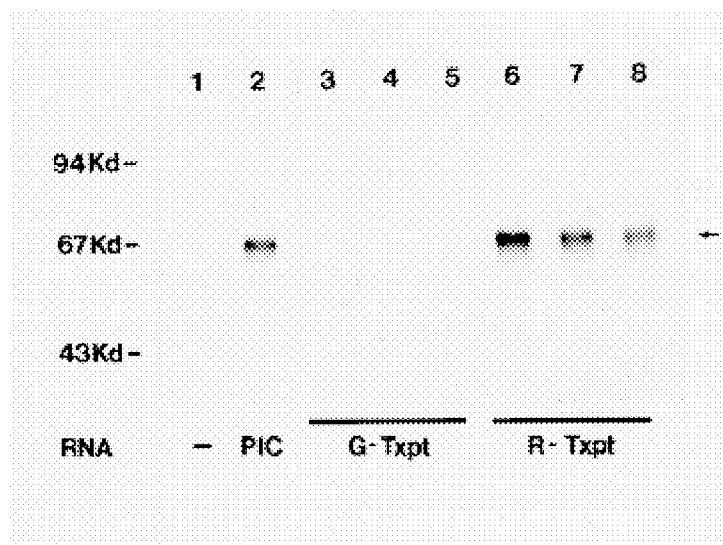
FIG. IB

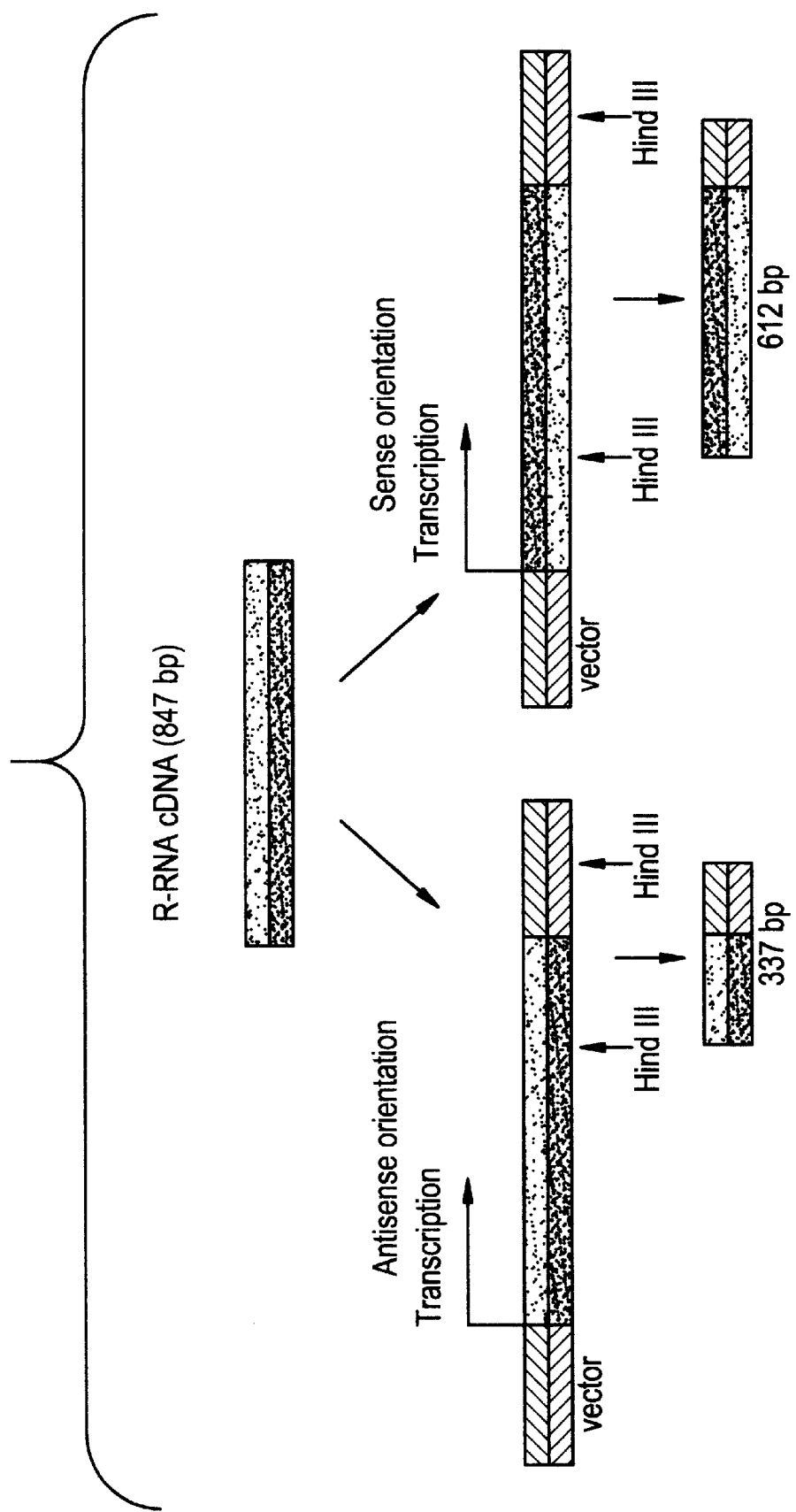

FIG. 3A

```
1    TGCACAAGGTGACATTTAAGAAAGTGTAGGCTTGTGCCAAAGGAGTATTTAGATGAAAATAACCCAGAGAATCAATTGGTGATCTTCAA    91
     A Q G D I L R K C R L V A K E Y L D E N N P E E S I G D L Q

92   TTCAATTTGAATATCTCAGAATAGAAAATAATATAGTATCACTTCTTGAACGCTCAGACAGGAAAGTTGTCATATTAATGGATAAGCTA   181
     F N L N I S E I E N N I V S L L E R S D R K V V I L M D K L

182  GATGAGGGCGTATGAACCGGATAATATAGGAATTGGAATCATTGCAGGTCTAGCATATGCATCTATTGAATTAAATCAAAAGCAAAATGC   271
     D E A Y E P D N I G I G I A G L A Y A S I E L N Q K A K C

272  ATTCGTCCAATAATTTTTTAAGGGATAATATATTAGGTCGCTATCAAAGGAAGATCCTGATTACTCGAGAAATATAGAGGGTCAAGTC    361
     I E P I I F L R D N I F R S L S K E D P D Y S R N I E G Q V

362  ATAAGGTTGCATTGGGACTGGGCACAACTCCTAAATGCTGTCAGCTAAAAGAATGAAAGTAGCATTTAAGCTAGATATTGAGAAAGATCAA   451
     I R L H W D W A Q L L M L S A K R M K V A F K L D I E K D Q

452  CGAGTTTGGGATAGATGCACAGCGGATGATCTTAAAGGGAGGAATGGTTTAAGCGATGTTGCAATTACCCTTTACCGGCCAGGGAT    541
     R V W D R C T A D D L K G R N G F K R C L Q F T L Y R P R D

542  TTACTATCATTGTGAATGAAGCTTTTTTCCGCATTCATTGAGAAGAGAATAGAGAAACTACTCATAAACACTGACCTAGAATATGCAGCCAAG   631
     L L S L L N E A F F S A F R E N R E T I I N T D L E Y A A K

632  TCAATTTCCATGGCCAGACTGAATGACTCTGAAAGAGATCTCTTCCTTCAATACAGGTTATAACTAGTGCATTCGTAGC           721
     S I S M A R L E D L W K E Y Q K I F P S I Q V I T S A F R S

722  ATTGAACCTGAATTAACAGTTTATACGTTGCTTAAAAAAATAGAAGCATCTTTCGAATTAATCGAAGAAAATGGAGATCCTAAAATAACG   811
     I E P E L T V Y T C L K K I E A S F E L I E E N G D P K I T

812  TCTGAAATACAGTTGTTAAAGGCAAGTGGAATTCCG   847
     S E I Q L L K A S G I L
```

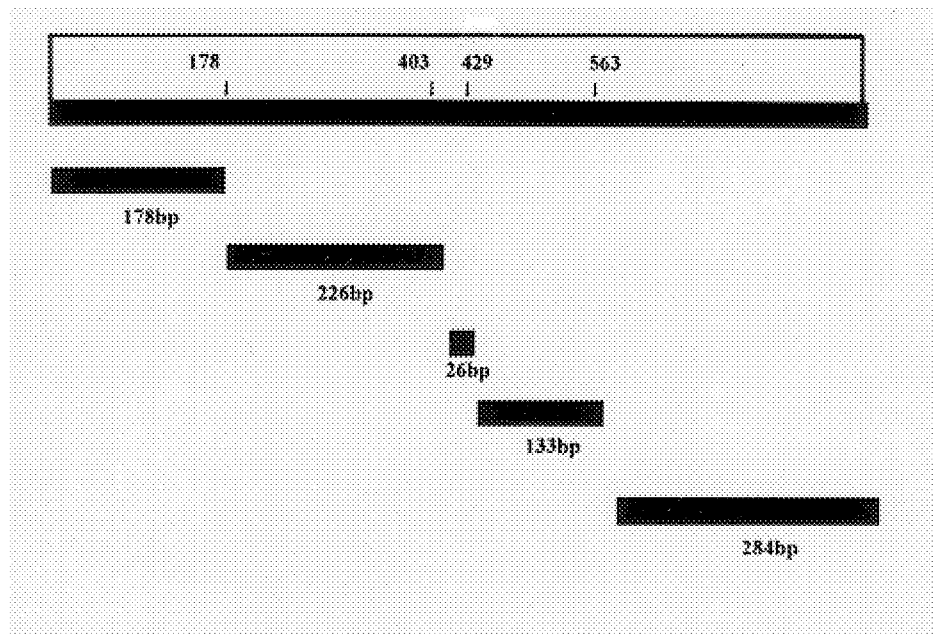
FIG. IIA
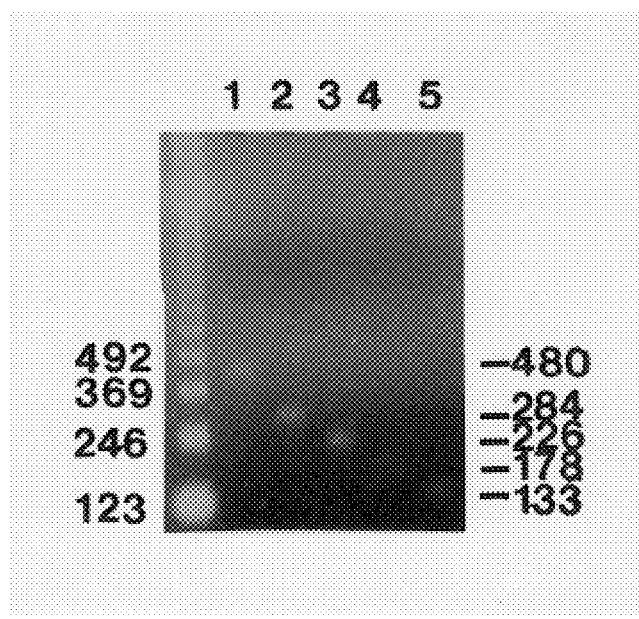
FIG. IIB

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
    (A) LENGTH: 847 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:1:

```
TGCACAAGGT GACATTTTAA GAAAGTGTAG GCTTGTCGCA AAGGAGTATT TAGATGAAAA    60

TAACCCAGAA GAATCAATTG GTGATCTTCA ATTCAATTTG AATATCTCAG AAATAGAAAA   120

TAATATAGTA TCACTTCTTG AACGCTCAGA CAGGAAAGTT GTCATATTAA TGGATAAGCT   180

AGATGAGGCG TATGAACCGG ATAATATAGG AATTGGAATC ATTGCAGGTC TAGCATATGC   240

ATCTATTGAA TTAAATCAAA AGCAAAATG CATTCGTCCA ATAATTTTTT TAAGGGATAA    300

TATATTTAGG TCGCTATCAA AGGAAGATCC TGATTACTCG AGAAATATAG AGGGTCAAGT   360

CATAAGGTTG CATTGGGACT GGGCACAACT CCTAATGCTG TCAGCTAAAA GAATGAAAGT   420

AGCATTTAAG CTAGATATTG AGAAAGATCA ACGAGTTTGG GATAGATGCA CAGCGGATGA   480

TCTTAAAGGG AGGAATGGTT TTAAGCGATG TTTGCAATTT ACCCTTTACC GGCCCAGGGA   540

TTTACTATCA TTGTTGAATG AAGCTTTTTT TTCCGCATTC AGAGAGAATA GAGAAACTAT   600

CATAAACACT GACCTAGAAT ATGCAGCCAA GTCAATTTCC ATGGCCAGAC TTGAAGATCT   660

CTGGAAAGAG TATCAGAAGA TCTTTCCTTC AATACAGGTT ATAACTAGTG CATTTCGTAG   720

CATTGAACCT GAATTAACAG TTTATACGTG CTTAAAAAAA ATAGAAGCAT CTTTCGAATT   780

AATCGAAGAA AATGGAGATC CTAAAATAAC GTCTGAAATA CAGTTGTTAA AGGCAAGTGG   840

AATTCCG                                                             847
```

(2) INFORMATION FOR SEQ ID NO:2:

(i) SEQUENCE CHARACTERISTICS:
    (A) LENGTH: 847 nucleotides
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO:2:

```
UGCACAAGGU GACAUUUUAA GAAAGUGUAG GCUUGUCGCA AAGGAGUAUU UAGAUGAAAA    60

UAACCCAGAA GAAUCAAUUG GUGAUCUUCA AUUCAAUUUG AAUAUCUCAG AAAUAGAAAA   120

UAAUAUAGUA UCACUUCUUG AACGCUCAGA CAGGAAAGUU GUCAUAUUAA UGGAUAAGCU   180

AGAUGAGGCG UAUGAACCGG AUAAUAUAGG AAUUGGAAUC AUUGCAGGUC UAGCAUAUGC   240

AUCUAUUGAA UUAAAUCAAA AGCAAAAUG CAUUCGUCCA AUAAUUUUUU UAAGGGAUAA    300

UAUAUUUAGG UCGCUAUCAA AGGAAGAUCC UGAUUACUCG AGAAAUAUAG AGGGUCAAGU   360

CAUAAGGUUG CAUUGGGACU GGGCACAACU CCUAAUGCUG UCAGCUAAAA GAAUGAAAGU   420

AGCAUUUAAG CUAGAUAUUG AGAAAGAUCA ACGAGUUUGG GAUAGAUGCA CAGCGGAUGA   480

UCUUAAAGGG AGGAAUGGUU UUAAGCGAUG UUUGCAAUUU ACCCUUUACC GGCCCAGGGA   540

UUUACUAUCA UUGUUGAAUG AAGCUUUUUU UUCCGCAUUC AGAGAGAAUA GAGAAACUAU   600

CAUAAACACU GACCUAGAAU AUGCAGCCAA GUCAAUUUCC AUGGCCAGAC UUGAAGAUCU   660

CUGGAAAGAG UAUCAGAAGA UCUUUCCUUC AAUACAGGUU AUAACUAGUG CAUUUCGUAG   720

CAUUGAACCU GAAUUAACAG UUUAUACGUG CUUAAAAAAA AUAGAAGCAU CUUUCGAAUU   780
```

```
AAUCGAAGAA AAUGGAGAUC CUAAAAUAAC GUCUGAAAUA CAGUUGUUAA AGGCAAGUGG    840

AAUUCCG                                                              847
```

(2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Cys Arg Leu Val Ala Lys Glu Tyr Leu Asp Glu Asn Asn Pro Glu Glu
1               5                   10                  15

Ser
```

(2) INFORMATION FOR SEQ ID NO:4:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
GAAAGTGTAG GCTTGTCGCA                                                 20
```

(2) INFORMATION FOR SEQ ID NO:5:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
CAGCATTAGG AGTTGTGCCC                                                 20
```

(2) INFORMATION FOR SEQ ID NO:6:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
CCTCATCTAG CTTATCCATT                                                 20
```

(2) INFORMATION FOR SEQ ID NO:7:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
ATCCGGTTCA TACGCCTCAT C                                        21
```

(2) INFORMATION FOR SEQ ID NO:8:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
CCTGCAATGA TTCCAATTCC                                          20
```

(2) INFORMATION FOR SEQ ID NO:9:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
ATTTAATTCA ATAGATGCAT AT                                       22
```

(2) INFORMATION FOR SEQ ID NO:10:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TATTGGACGA ATGCATTTTG                                          20
```

(2) INFORMATION FOR SEQ ID NO:11:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
TCTTCCTTTG ATAGCGACCT                                          20
```

(2) INFORMATION FOR SEQ ID NO:12:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
GAGTAATCAG GATCTTTCTT                                          20
```

(2) INFORMATION FOR SEQ ID NO:13:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CCTTATGACT TGACCCTCTA TA                                      22

(2) INFORMATION FOR SEQ ID NO:14:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

AGGAGTTGTG CCGACTCCCA                                        20

(2) INFORMATION FOR SEQ ID NO:15:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TTCATTCTTT TAGCTGACAG C                                       21

(2) INFORMATION FOR SEQ ID NO:16:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

CTCAATATCT AGCTTAAATG                                        20

(2) INFORMATION FOR SEQ ID NO:17:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GTTTTACGTA AGCAGGTTAT                                        20

(2) INFORMATION FOR SEQ ID NO:18:

(i) SEQUENCE CHARACTERISTICS:
        (A) LENGTH: 20 nucleotides

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

AATGTGTAGT TGCGTACTGA                                             20

(2) INFORMATION FOR SEQ ID NO:19:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CCTCGGTCCC CCCTCGTCCC                                             20
```

CELL GROWTH-CONTROLLING OLIGONUCLEOTIDES

This invention was made with Government support under Grant No. RO1-CA-42717, awarded by the National Institutes of Health. The Government has certain rights in the invention.

FIELD OF THE INVENTION

PKR is a dsRNA-dependent (double stranded RNA-dependent) protein kinase which is implicated in the regulation of several cellular processes including cell proliferation. Previous studies using embryonic mouse 3T3-F442A cells have indicated that PKR undergoes phosphorylation and activation in vivo. This activation of PKR has been attributed to a subset of poly(A)+—rich cellular RNA having sufficient secondary structure to interact with the kinase. The present invention provides a partial cDNA corresponding to the RNA containing double stranded regions, which, when transcribed in vitro, gives rise to an RNA transcript that activates PKR. An approximately 226–252 bp nucleotide (nt) sequence responsible for activation of PKR (the activation sequence) has been identified within the cDNA and isolated. Antisense oligonucleotides corresponding to specific portions of the 226 nt cDNA fragment stimulate proliferation of human hematopoietic cells and mouse fibroblasts in culture.

BACKGROUND OF THE INVENTION

The dsRNA-dependent eIF-2α kinase (hereinafter "PKR"), also known as DAI, p68, dsI and dsRNA-PK (Clemens, et al., 1993, *J. Interferon Res.* 13: 241), is an interferon (IFN)-induced enzyme that mediates, in part, the antiviral and antiproliferative effects of IFN (Pestka, et al., 1987, *Ann. Rev. Biochem.* 56: 727–777; Hovanessian, et al., 1989, *J. Interferon Res.* 9: 641–647). Other studies have indicated that PKR may also be involved in the regulation of cell growth and differentiation of some cells, function as a tumor suppressor (Meurs, et al., 1993, *Proc. Nat. Acad. Sci.* 90: 232–236; Petryshyn, et al., 1994, *J. Biol. Chem.* 259: 14736–14742; Petryshyn, et al., 1988, *Proc. Natl. Acad. Sci.* 85: 1427–1431; Judware, et al., 1991, *Mol. Cell. Biol.* 11: 3259–3267; Koromilas, et al., 1992, *Science* 257: 1685–1689; Chong, et al., 1992, *EMBO J.* 11: 1553–1562) and modulate signal transduction (Kumar, et al., 1994, *Proc. Natl. Acad. Sci.* 91: 6288–6292; Maran, et al., 1994, *Science* 265: 789–792).

Still other studies have indicated that PKR may be involved in regulating programed cell death (apoptosis) (Young et al., 1996 *Proc. Nat. Acad. Sci.* 93:12451–12455). The mechanism by which PKR controls protein synthesis in vitro is reasonably understood (Lebleu, et al., 1976, *Proc. Natl. Acad. Sci.* 73: 3107–3111; Farrell, et al., 1977, *Cell* 11: 187–200; Levin, et al., 1978, *Proc. Natl. Acad. Sci.* 75: 1121–1125; Samuel, 1979, *Proc. Natl. Acad. Sci.* 76: 600–604; Petryshyn, et al., 1983, *Methods Enzymol.* 99: 346–362). In the presence of ng/ml levels of dsRNA, ATP and divalent cations, the enzyme undergoes autophosphorylation which converts it from a latent to an active protein kinase (Hovanessian, 1989, *J. Interferon Res.* 9: 641–647; Lebleu, et al., 1976). The autophosphorylation and activation of PKR is prevented by high concentrations of dsRNA (Farrel, et al., 1977; Hunter, et al., 1975, *J. Biol. Chem.* 250: 409–417). Upon activation, the kinase catalyzes the phosphorylation of the a-subunit (38 kDa) of the eukaryotic initiation factor 2 (eIF-2α) (Lebleu, et al., 1976; Farrel, et al., 1977; Levin, et al. 1978; Samuel, 1979; Petryshyn, et al., 1983). The phosphorylation of eIF-2α prevents the ability of eIF-2 to exchange GDP for GTP which is catalyzed by eIF-2β (Matts, et al., 1984, *J. Biol. Chem.* 259: 6708–6711; Rowlands, et al., 1988, *J. Biol. Chem.* 263: 5526–5533). This cascade of reactions results in the inhibition of protein synthesis (London, et al., 1987, *The Enzymes Vol.* 18; Hershey, 1989, *J. Biol. Chem.* 264: 20823–20826).

Duplex RNA molecules such as reovirus dsRNA and poly(I)•poly(C) (PIC) are well established activators of PKR (Hovanessian, 1989), but the details of the activation process are not fully understood (Galabru, et al., 1989, *Eur. J. Biochem.* 178: 581–589; Kostura, et al., 1989, *Mol. Cell. Biol.* 9: 1576–1586; Kitajewski, et al., 1986, *Cell* 45: 195–200). Moreover, several single stranded (ss) viral RNAs including adenovirus VA1 RNA (Schneider, et al., 1987, *Ann. Rev. Biochem.* 56: 317–332; Furtado, et al., 1989, *J. Virol.* 63: 3423–3434; Ghadge, et al., 1994, *J. Virol.* 68: 4137–4151), Epstein Barr Virus EBER-1 RNA (Clarke, et al., 1991, *Nucleic Acids Res.* 19: 243–248) and HIV-1 mRNA (Edery, et al., 1989, *Cell* 56: 303–312; Sen Gupta, et al., 1989, *Nucl. Acids Res.* 17: 969–978; Roy, et al., 1991, *J. Viol.* 65: 632–640; Judware, et al., 1993, *J. Interferon Res.* 13: 153–160) have been demonstrated to contain secondary structures which interact and modulate the activity of PKR. Relatively little is known about the mechanism by which structural elements within these RNAs interact with the kinase but studies have indicated that the amino terminal portion of the protein is important for RNA binding (Feng, et al., 1992, *Proc. Natl. Acad. Sci.* 89 5447–5451; Manche, et al., 1992, *Mol. Cell Biol.* 12: 5238–5248; Petryshyn, et al., 1994, Progress in *Molecular and Subcellular Biology Vol.* 14; Chong, et al., 1992). of significance are the findings that eIF-2α undergoes phosphorylation in response to addition of cytoplasmic mRNA (Baum, et al., 1983, *Biochem. Biophys. Res. Commun* 114: 41–49) or polysomal RNA (Pratt, et al., 1988, *Nucl. Acids Res.* 16: 3497–3510) prepared from uninfected cells and that this phosphorylation is prevented by high concentrations of poly(I)•poly(C) (Baum, et al., 1983; Pratt, et al., 1988). In addition, altered levels of eIF-2 phosphorylation and PKR activity have been reported in some cells subjected to heat-stress conditions (Dubois, et al., 1991, *J. Biol. Chem.* 266: 9707–9711). Other studies have indicated that the mRNA for PKR itself is capable of facilitating the phosphorylation of PKR (Thomis, et al., 1993, *J. Virol.* 67: 7695–7700). These observations suggest that some cellular RNAs may regulate the activity of PKR and raise the possibility that the enzyme has a regulatory role in uninfected cells (Petryshyn, et al., 1994). This is supported by the finding of an accumulation of dsRNA capable of activating PKR in embryonal carcinoma cells that have been induced to differentiate but not in uninduced cells (Belkumeur, et al., 1993, *Mol. Cell. Biol.* 13: 2846–2857). To date, however, the extent and nature of the cellular RNA(s) that mediate the activation of PKR in uninfected cells remain to be identified.

The role of IFN and PKR in the regulation of growth and differentiation of mouse 3T3-F442A cells has recently been investigated. 3T3-F442A cells spontaneously produce and secrete IFN and exhibit a pattern of PKR phosphorylation which is related to specific stages of growth (Petryshyn, et al., 1984). PKR is phosphorylated both in vivo and in vitro in the absence of viral infection or added dsRNA (Petryshyn, et al., 1988). The phosphorylation of PKR is concomitant with increased phosphorylation of eIF-2α, diminished eukaryotic initiation factor 2-β (eIF-2β) activity and a marked reduction in protein synthesis (Petryshyn, et al., 1996, *Arch. Biochem. Biophys.* 328: 290–297).

A subset of poly(A)⁺—rich cytoplasmic RNA that is responsible for activation of PKR in 3T3-F442A cells ("Regulatory RNA" or "R-RNA") has recently been isolated (Li, et al., 1991, *Eur. J. Biochem.* 195: 41–48) although the nature and exact number of RNAs comprising the R-RNA activity was not determined.

The present invention provides a partial cDNA of about 850 base pairs corresponding to a single and specific cellular R-RNA which, when transcribed in vitro, gives rise to an RNA transcript which retains its property to activate PKR. In addition, the present invention provides a 226–252 nucleotide fragment of the partial cDNA which corresponds to that portion of R-RNA necessary for PKR activation ("the activation sequence"). An antisense molecule to the 226–252 nt cDNA fragment as well as a number of smaller antisense oligonucleotides all of which bind to the sense strand of the R-RNA and thus prevent activation of PKR are also provided. The present invention further provides methods of stimulating the proliferation of hematopoietic cells and fibroblast cells in culture.

SUMMARY OF THE INVENTION

The present invention provides a portion of a cDNA corresponding to a specific dsRNA known as Regulatory RNA (R-RNA) which interacts with PKR through its double stranded RNA regions and stimulates autophosphorylation of PKR. The subject partial cDNA molecule is approximately 847 nucleotides in length and has the sequence set forth in SEQ ID NO:1. The present invention also provides a 225–252 nt fragment of the partial R-RNA cDNA, which is responsible for the activation of PKR (herein referred to as the activation sequence).

In one aspect of the invention, there is provided an R-RNA from which the subject cDNA may be reverse transcribed. The sequence of the subject R-RNA is set forth in SEQ ID NO:2 and is useful in cell cultures for purposes of inhibition of cell proliferation (expansion). For example, the subject R-RNA may be administered ex vivo to bone marrow cells isolated from patients with hematological cancers. After sufficient time, the bone marrow cells are transplanted back into the donor patient.

In another aspect of the invention, there is provided an antisense molecule corresponding to the sense strand of the subject R-RNA. The subject antisense molecule binds to R-RNA, thereby interfering with the activation of PKR by R-RNA. The subject antisense molecule is therefore useful for preventing the autophosphorylation of PKR and the inhibition of cell division resulting from such autophosphorylation.

In one embodiment of the invention, there is provided an isolated nucleic acid molecule consisting of a nucleotide sequence or complementary to a nucleotide sequence as set forth in SEQ ID NO:1 or having at least 50% similarity or complementarity thereto.

In another embodiment of the invention, there is provided an isolated nucleic acid molecule consisting of a nucleotide sequence or complementary to a nucleotide sequence as set forth in SEQ ID NO:2 or having at least 50% similarity or complementarity thereto.

The present invention further provides an isolated nucleic acid molecule consisting of or complementary to nucleotides 178–430 of SEQ ID NO:1 or having at least 50% similarity or complementarity thereto.

In another embodiment of the invention, there is provided an isolated nucleic acid molecule which hybridizes to the activation sequence of the R-RNA i.e., nucleotides 178–430 of SEQ ID NO:2 under medium to high stringency conditions.

In another embodiment, an isolated nucleic acid molecule consisting of or complementary to nucleotides 263–283 of SEQ ID NO:1 or having at least 50% similarity or complementarity thereto is provided.

An isolated nucleic acid molecule which hybridizes to nucleotides 263–283 of SEQ ID NO:2 under medium to high stringency conditions is yet another embodiment of the present invention.

In a further embodiment of the present invention, there is provided an isolated nucleic acid molecule consisting of or complementary to nucleotides 374–393 of SEQ ID NO:1 or having at least 50% similarity or complementarity thereto.

In yet another embodiment of the invention, there is provided an isolated nucleic acid molecule which hybridizes to nucleotides 374–393 of SEQ ID NO:2 under medium to high stringency conditions.

In accordance with the present invention, oligonucleotides complementary to specific portions of the subject R-RNA sense strand are also provided. By "specific portions" is meant specific nucleotide sequences found within the R-RNA activation sequence. The subject antisense oligonucleotides of the present invention comprise at least eight or nine nucleotides which are complementary to at least eight or nine contiguous nucleotides of nucleotides 178–430 as set forth in SEQ ID NOs:1 or 2. Other antisense oligonucleotides include oligonucleotides comprising at least eight or nine nucleotides which are complementary to: at least eight or nine contiguous nucleotides of nucleotides 263–283 as set forth in SEQ ID NOs:1 or 2, or at least eight or nine contiguous nucleotides of nucleotides 374–393 as set forth in SEQ ID NOs: 1 or 2. Larger antisense oligonucleotides of, for example, 10 to greater than 25 nucleotides are also contemplated by the present invention.

In one embodiment of the invention, the antisense oligonucleotide comprises the nucleotide sequence set forth in SEQ ID NO:6. In another embodiment of the invention, the antisense oligonucleotide comprises at least eight contiguous nucleotides derived from the sequence set forth in SEQ ID NO:6.

In another embodiment of the invention, the antisense oligonucleotide has the nucleotide sequence set forth in SEQ ID NO:7. In another embodiment of the invention, the antisense oligonucleotide comprises at least eight contiguous nucleotides derived from the sequence set forth in SEQ ID NO:7.

In yet another embodiment of the invention, the antisense oligonucleotide has the nucleotide sequence set forth in SEQ ID NO:10. In another embodiment of the invention, the antisense oligonucleotide comprises at least eight contiguous nucleotides derived from the sequence set forth in SEQ ID NO:10.

In still another embodiment of the invention, the antisense oligonucleotide has the nucleotide sequence set forth in SEQ ID NO:14. In another embodiment of the invention, the antisense oligonucleotide comprises at least eight contiguous nucleotides derived from the sequence set forth in SEQ ID NO:14.

The present invention also provides a method of inhibiting the activation of PKR in a cell culture. The method comprises contacting said cell culture with an effective amount of at least one of an isolated nucleic acid molecule complementary to SEQ ID NO:1, an isolated nucleic acid molecule complementary to nucleotides 178–430 of SEQ ID NO:1, an isolated nucleic acid molecule complementary to nucleotides 263–283 of SEQ ID NO:1, an isolated nucleic acid molecule complementary to nucleotides 374–393 of SEQ ID NO:1; an oligonucleotide having the sequence set forth in SEQ ID NO:6 or at least eight contiguous nucleotides of SEQ ID NO:6, an oligonucleotide having the sequence set forth in SEQ ID NO:7 or at least eight contiguous nucloetides of SEQ ID NO:7, an oligonucleotide having the sequence set forth in SEQ ID NO:10 or at least eight contiguous nucleotides of SEQ ID NO:10, or an oligonucleotide having the sequence set forth in SEQ ID NO:14 or at least eight contiguous nucleotides of SEQ ID NO: 14.

In another aspect of the invention, compositions for stimulating cell proliferation (expansion) in cell cultures are provided. The compositions comprise at least one of the subject isolated nucleic acid molecules or antisense oligonucleotides admixed with a pharmaceutically acceptable carrier.

In another aspect of the present invention, kits are provided which comprise at least one of the subject isolated nucleic acid molecules or antisense oligonucleotides and a pharmaceutically acceptable carrier. The pharmaceutical acceptable carrier may be packaged separately or admixed with the subject isolated nucleic acid molecules or oligonucleotides.

A method of stimulating cell proliferation in a cell culture by contacting the cell culture with an effective amount of at least one of the subject isolated nucleic acid molecules or oligonucleotides is also provided. For example, cells which are typically difficult to grow and regenerate such as nerve, muscle or brain cells, can be expanded by such a method. In addition, epithelial cells can be expanded by contacting cultured cells with an effective amount of at least one of the subject antisense fragments or oligonucleotides prior to using the cultured cells in a skin grafting procedure.

A method of inhibiting cell proliferation in bone marrow cells obtained from a patient suffering from a hematological cancer is also provided by the present invention. The method comprises isolating a bone marrow sample from a patient suffering from a hematological cancer, contacting the cells in said sample with at least one of an R-RNA having the sequence set forth in SEQ ID NO:2, a portion of an R-RNA having nucleotides 178–430 of SEQ ID NO:2, a portion of an R-RNA having nucleotides 263–283 of SEQ ID NO:2, or a portion of an R-RNA having nucleotides 374–393 of SEQ ID NO:2, and after a sufficient time, transplanting said sample back into the donor patient.

In another aspect of the invention, a method for promoting expansion of pluripotent progenitor cells is provided. The method comprises obtain bone marrow cells from a patient and contacting said cells with an effective amount of an oligonucleotide having the nucleotide sequence set forth in SEQ ID NO:10.

The present invention further provides a method for promoting expansion of hematopoietic stem cells in a cell culture which comprises obtaining peripheral blood from a patient, isolating mononuclear cells and contacting said mononuclear cells with an effective amount of an oligonucleotide having the nucleotide sequence set forth in SEQ ID NO:10.

In a further aspect of the invention, a method for promoting neutrophil expansion and development from a neutrophil depleted marrow cell culture is provided. In one embodiment, marrow from a patient suffering from severe congenital neutropenia (SCN) is obtained and contacted with an effective amount of an oligonucleotide having the sequence set forth in SEQ ID NO:10. After a sufficient time, the marrow cells are transplanted back into the patient.

A method for expanding hematopoietic cells in umbilical cord blood is also provided. The method comprises contacting a sample of the cord blood with at least one oligonucleotide selected from the group consisting of an oligonucleotide having the sequence set forth in SEQ ID NO:8, an oligonucleotide having at least eight contiguous nucleotides as set forth in SEQ ID NO:8, an oligonucleotide having the sequence set forth in SEQ ID NO:10 or an oligonucleotide having at least eight contiguous nucleotides as set forth in SEQ ID NO:10.

The present invention further provides pharmaceutical compositions comprising the subject nucleic acid fragments and oligonucleotides. Such pharmaceutical compositions are useful in practicing the methods of the present invention. Kits which comprise at least one of the subject isolated nucleic acid molecules or oligonucleotides and a pharmaceutically acceptable carrier are also provided.

BRIEF DESCRIPTION OF THE DRAWINGS

FIG. 1A is an autoradiogram which depicts the effect of the R-RNA transcript on PKR phosphorylation. All RNA transcripts were gel purified and added to protein kinase assays containing 3T3-F442A S10 extracts or purified 3T3-PKR to give the final concentrations indicated. The reaction mixtures contained the following additions: Lane 1, no RNA; Lane 2, 150 ng/ml poly(I)•poly(C)(PIC); Lanes 3,5, 7,9 and 11, 5.0 µg/ml RNA from clones R-12, R-18, R-33, R-15 and R101 as indicated; Lanes 4,6,8,10 and 12, 0.50 µg/ml RNA from clones indicated. The migration position and molecular weights (×10$^3$) of protein standards, phosphorylase (94 kDa), bovine serum albumin (67 kDa) and ovalbumin (43 kDa) are indicated on the left. The arrow indicates the position of PKR.

FIG. 1B is an autoradiogram depicting the effect of the R-RNA transcript on PKR phosphorylation under the same conditions as depicted in FIG. 1A. Lane 1, no RNA; Lane 2, 150 ng/ml poly(I)•poly(C) (PIC); Lanes 3–5, 2.5 µg/ml (Lane 3), 1.25 µg/ml (Lane 4) and 625 ng/ml (Lane 5) of the globin RNA transcript (G-Txpt); Lanes 6–8, 2.5 µg/ml (Lane 6) 1.25 µg/ml (Lane 7) and 625 ng/ml (Lane 8) of the R-RNA transcript (R-Txpt). The migration position and molecular weights (×10$^3$) of protein standards are as in FIG. 1A. The arrow indicates the position of PKR.

FIG. 2A is a schematic diagram of the 847 bp R-RNA cDNA and indicates the constructs prepared, the location of the Hind III sites and the size of the DNA fragments expected from both orientations. The orientations have been designated as antisense orientation (i.e., complementary to the authentic R-RNA, the resulting transcript (Txpt) hybridizes to the A$^+$-RNA) and sense orientation.

FIG. 3A depicts the nucleotide sequence (SEQ ID NO:1) and alignment of the isolated R-RNA cDNA fragment. The deduced amino acid sequence is shown below the nucleotide sequence. The amino acid sequence shown underlined was used to generate antiserum.

FIG. 11A is a schematic diagram indicating the Alu I restriction map of the 847 bp R-RNA cDNA. Five Alu I fragments were predicted from the sequence.

FIG. 11B is a photograph of an ethidium bromide stained agarose gel through which were electrophoresed Alu I fragments obtained from the digestion of the 847 bp R-RNA cDNA. The 26 bp fragment is not shown. Lane 1, a 480 bp DNA marker; lane 2, Alu 284 bp; lane 3, Alu 226 bp; lane 4, Alu 178 bp; lane 5, Alu 133 bp. Migration position of DNA of known size ladder is shown on far left lane.

DETAILED DESCRIPTION OF THE INVENTION

Figure 2B:
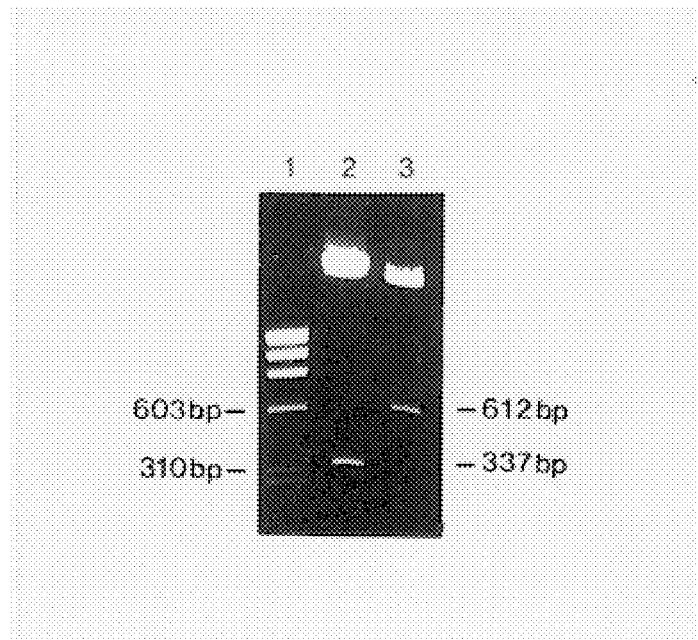
FIG. 2B is a photograph of an ethidium bromide stained agarose gel after electrophoresis of Hind III digested pGEM3Zf(±). Lane 1 contains Hae III digested Phi ×174 DNA as a marker. Lane 2 contains a 337 bp fragment as expected for the construct in the antisense orientation. Lane 3 contains a 612 bp fragment as expected for the construct in the sense orientation.

The present invention provides both a regulatory RNA (R-RNA) and a partial cDNA corresponding to the R-RNA. The R-RNA interacts with and stimulates autophosphorylation of PKR. In accordance with the present invention, the R-RNA may be used in different cell cultures in order to inhibit cell proliferation. For example, inhibition of cancerous cells in a bone marrow cell culture may be obtained by contacting a bone marrow cell culture isolated from a patient suffering from a hematological cancer with the R-RNA of the present invention. The nucleotide sequence of the subject R-RNA is set forth in SEQ ID NO:2.

Also in accordance with the present invention, a portion of the R-RNA responsible for activation of PKR has been identified. The activation sequence is approximately 226–252 nt in length and is made up of nucleotides 178–404 and can include an additional 26 nucleotides for a fragment comprising nucleotides 178–430 of SEQ ID NO:2. Thus, the R-RNA activation sequence alone may be used in a method of inhibiting cell proliferation in different cell cultures.

The present invention also provides a partial cDNA corresponding to the R-RNA. The cDNA sequence is approximately 847 nt long and has the sequence set forth in SEQ ID NO:1. In addition, sequence corresponding to the R-RNA activation sequence located at nucleotides 178–404 or 178–430 of SEQ ID NO:1 is also provided. Sequences complementary to the sense strand of the R-RNA cDNA, including the activation sequence or portions thereof, are useful in methods of inhibiting the activation of PKR and promoting cell expansion in cell cultures.

For example, an isolated nucleic acid fragment having either the nucleotide sequence as set forth in SEQ ID NOs:1 or 2, or nucleotides 178–404 or 178–430 of SEQ ID NOs:1 or 2 or having at least a 50% similarity thereto is useful in methods of inhibiting cell expansion in a cell culture. An isolated nucleic acid fragment complementary to the nucleotide sequence as set forth in SEQ ID NOs:1 or 2 or having at least a 50% complementarity is useful in promoting cell proliferation in cell cultures.

A nucleotide sequence which is complementary to the 226–252 nt fragment corresponding to nucleotides 178–404 or 178–430 of SEQ ID NOs:1 or 2 or having at least a 50% complementarity thereto is a preferred fragment for inhibiting the activation of PKR and promoting cell proliferation in cell cultures. Other preferred fragments include a nucleotide sequence which is complementary to nucleotides 263–283 of SEQ ID NOs:1 or 2 or having at least a 50% complementarity thereto, and a nucleotide sequence which is complementary to nucleotides 374–393 of SEQ ID NOs:1 or 2 or having at least a 50% complementarity thereto.

Other nucleotide sequences which hybridize to portions of the activation sequence of the subject R-RNA are also contemplated by the present invention. For example, isolated nucleic acid molecules which hybridize to nucleotides 178–430 of SEQ ID NO:2 under medium to high stringency conditions are contemplated as are isolated nucleic acid molecules which hybridize to nucleotides 263–283 of SEQ ID NO:2 under medium to high stringency conditions. Also contemplated by the present invention are isolated nucleic acid molecules which hybridize to nucleotides 374–393 of SEQ ID NO:2 under medium to high stringency conditions. Such isolated nucleic acid molecules are useful in promoting cell proliferation when used in conjunction with cell culture methods.

Preferred percentage similarities or complementarity include 80%, 85%, 90%, 92–95%, 96–98% and 99–100%. However, nucleic acid molecules having at least 50% similarities to SEQ ID NO:1 and portions thereof as defined herein and which can be used in various reverse transcription reactions in order to produce an R-RNA which activates PKR and inhibits cell proliferation are within the scope of the present invention. Similarly, nucleic acid molecules having at least 50% complementarities to SEQ ID NO:1 and portions thereof as defined herein and which inhibit the activation of PKR and stimulate cell proliferation are within the scope of the present invention.

As used herein, hybridization under medium or high stringency conditions are as defined in Maniatis et al. 1982 *Molecular Cloning*, Cold Spring Harbor Laboratory, N.Y., at pages 387–389, and especially paragraph 11 which is herein incorporated by reference. A low stringency is defined as being in 4–6×SSC/1% (w/v) SDS at 37–45° C. for 2–3 hours. Medium stringency conditions are considered herein to be 1–4×SSC/0.5%–1% (w/v) SDS at greater than or equal to 45° C. for 2–3 hours. High stringency conditions are considered herein to be 0.1–1×SSC/0.1–1% (w/v) SDS at greater than or equal to 60° C. for 1–3 hours. As used herein, medium to high stringency conditions refer to conditions which are either medium stringency conditions, high stringency conditions, or conditions between medium and high stringency.

A cDNA corresponding to R-RNA can be provided by first fractionating poly(A)$^+$ by cellulose chromatography followed by cDNA synthesis using any number of widely known methods and commercially available kits. Identification of a cDNA corresponding to an R-RNA and isolation of the R-RNA may be achieved by protein kinase assays where R-RNA transcribed from an isolated cDNA clone placed under the control of a promoter in an expression vector, facilitates phosphorylation of the 67 KDa phosphoprotein known as PKR. Protein kinase assay methodologies are widely known and can be found e.g., in Petryshyn et al., 1983 *Methods Enzymol.* 9:346–362 and Petryshyn et al., 1988 *Proc. Natl. Acad. Sci. U.S.A.* 85:1427–1431. Specific fragments of the R-RNA cDNA may be isolated using various restriction enzymes which are widely available. Such enzymes have known restriction sites which can be mapped to the R-RNA cDNA. For example, the R-RNA cDNA may be restricted with HindIII to render a 337 bp and 612 bp fragment (FIG. 2A). It may also be used to render fragments of 284, 226, 178, 133 and 26 base pairs (FIG. 11A).

The present invention also provides oligonucleotides which are useful for inhibiting the activation of PKR and stimulating cell proliferation under cell culture conditions. The subject oligonucleotides of the present invention comprise at least eight or nine nucleotides which are complementary to at least eight or nine contiguous nucleotides of nucleotides 178–430 as set forth in SEQ ID NOs:1 or 2. Other antisense oligonucleotides include oligonucleotides comprising at least eight or nine nucleotides which are complementary to: at least eight or nine contiguous nucleotides of nucleotides 263–283 as set forth in SEQ ID NOs:1 or 2, or at least eight or nine contiguous nucleotides of nucleotides 374–393 as set forth in SEQ ID NOs: 1 or 2. Larger antisense oligonucleotides of, for example, 10 to greater than 25 nucleotides are also contemplated by the present invention. The skilled artisan is cognizant of the many different methods in which to make such oligonucleotides and methods for testing whether such oligonucleotides have the capacity to inhibit activation of PKR and stimulate cell proliferation under cell culture conditions. Methods for testing whether oligonucleotides inhibit the activation of PKR and stimulate cell proliferation are provided in the working examples e.g., protein kinase assays and cell culture studies.

The lower limit to the length of a subject oligonucleotide (eight or nine nucleotides) is based upon well known principles of deoxyribonucleotide and ribonucleotide binding. As is known by those of skill in the art, usually at least eight or nine nucleotides are necessary to provide stable binding among ribonucleotide and deoxyribonucleotide sequences. Since the methods of the present invention involve use of the subject oligonucleotides in order to bind to R-RNA, a lower limit of eight or nine nucleotides is contemplated for the subject oligonucleotides.

The present invention also provides specific oligonucleotides which comprise nucleotides from the antisense strand of SEQ ID NOs:1 or 2. For example, an oligonucleotide may comprises the sequence set forth in SEQ ID NO:6 or at least eight contiguous oligonucleotides derived from the sequence set forth in SEQ ID NO:6. Other oligonucleotides provided by the present invention include an oligonucleotide comprising the sequence set forth in SEQ ID NO:7 or at least eight contiguous oligonucleotides derived from the sequence set forth in SEQ ID NO:7, an oligonucleotide comprising the sequence set forth in SEQ ID NO:8 or at least eight contiguous oligonucleotides derived from the sequence set forth in SEQ ID NO:8, and an oligonucleotide comprising the sequence set forth in SEQ ID NO:14 or at least eight contiguous oligonucleotides derived from the sequence set forth in SEQ ID NO:14.

In a preferred embodiment, the oligonucleotide comprises the sequence set forth in SEQ ID NO:8 or at least eight contiguous oligonucleotides derived from the sequence set forth in SEQ ID NO:8, In another preferred embodiment, the oligonucleotide comprises the sequence set forth in SEQ ID NO:10 or at least eight contiguous oligonucleotides derived from the sequence set forth in SEQ ID NO:10.

Modifications to the oligonucleotides set forth in SEQ ID NOs:6, 7,8, 10 and 14 which bind to R-RNA and which maintain the characteristic property of interfering with the interaction of R-RNA to PKR are also within the scope of the present invention. Such modifications include insertions, deletions and substitutions of one or more nucleotides.

The isolated nucleic acid fragments and oligonucleotides of the present invention are DNA or RNA, or hybrids of DNA and RNA. For example, the subject nucleic acid fragments and oligonucleotides can comprise: all RNA; all DNA; RNA interspersed with 2'—O-methyl RNA, and so on. The nucleic acid fragments and oligonucleotides comprise the bases guanine (G), adenine (A), thymine (T), cytosine (C) or uracil (U) in the nucleotides, or any nucleotide analog that is capable of binding to R-RNA. Nucleotide analogs include pseudocytidine, isopseudocytidine, imidazole, 3-aminophenyl-imidazole, 2'—O-methyl-adenosine, 7-deazadenosine, 7-deazaguanosine, 7-deazaxanthosine, 4-acetylcytidine, 5-(carboxy-hydroxylmethyl)-uridine, 2'—O-methylcytidine, 5-carboxymethylaminomethyl-2-thioridine, 5-carboxymethylamino-methyluridine, dihydrouridine, 2'—O-methyluridine, pseudouridine, 2'—O-methyl-pseudouridine, beta, D-galactosylqueosine, 2'—O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, 5-methyluridine, N6-methyl-adenosine, 7-methylguanosine, 5-methylamino-methyluridine, 5-methoxyaminomethyl-2-thiouridine, β-D-mannosylqueosine, 5-methoxycarbonylmethyluridine, 5-methoxyuridine, 2-methyl-thio-N6-isopentenyladenosine, N-(9-beta- Dribofuranosyl-2-methylthiopurine-6-yl)-carbamoyl) threonine, N-(9-beta-D-ribofuranosylpurine-6-yl)-N-methylcarbamoyl)threonine and thioguanosine.

Either ribose or deoxyribose sugars can be used with the above-listed analogs. Modified sugars, such as 2'—O-methyl ribose, are also contemplated. Nucleotides bases in an a-anomeric conformation can also be used in the isolated nucleic acids and oligonucleotides of the present invention.

Preferred nucleotides analogs are unmodified G, A, T, C and U nucleotides; pyrimidine analogs with lower alkyl, alkynyl or alkenyl groups in the 5 position of the base and purine analogs with similar groups in the 7 or 8 position of the base. Especially preferred nucleotide analogs are 5-methylcytosine, 5-methyluracil, diaminopurine, and nucleotides with a 2'—O-methylribose moiety in place of ribose or deoxyribose. As used herein lower alkyl, lower alkynyl and lower alkenyl contain from 1 to 6 carbon atoms and can be straight chain or branched. These groups include methyl, ethyl, propyl, isopropyl, butyl, isobutyl, tertiary butyl, amyl, hexyl and the like. A preferred alkyl group is methyl.

The isolated nucleic acid molecules of the present invention may be generated from larger nucleic acid fragments having excess sequence on either or both 3' and 5' ends removed via exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g. Promega Biotech, "Erase-A-Base" system. Alternatively, PCR primers can be defined to allow direct amplification of the subject nucleic acid fragments.

The subject nucleic acid molecules and oligonucleotides of the present invention can also be made by any of a myriad of procedures known for making DNA or RNA oligonucleotides. For example, such procedures include enzymatic synthesis and chemical synthesis.

Enzymatic methods of DNA oligonucleotides synthesis frequently employ Klenow, T7, T4, Taq or *E. coli* DNA polymerase as described in Sambrook et al. 1989, in *Molecular Cloning: A Laboratory Manual*, Cold Spring Harbor, N.Y. Enzymatic methods of RNA oligonucleotide synthesis frequently employ SP6, T3 or T7 RNA polymerase as described in Sambrook et al., 1989. Reverse transcriptase can also be used to synthesize DNA from RNA (Sambrook et al. 1989). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally linear oligonucleotides can be prepared by polymerase chain reaction (PCR) techniques as described, for example, by Saiki et al., 1988, *Science* 239: 487.

Chemical synthesis of linear oligonucleotides is well known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann, et al. (1990, *Chemical Reviews* 90: 543–584) provide references and outline procedures for making oligonucleotides with modified bases and modified phosphodiester linkages.

Synthetic linear oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104: 976; Viari, et al., 1987, *Biomed. Enciron. Mass Spectrom.* 14: 83; Grotjahn et al., 1982, *Nuc. Acid Res.* 10: 4671). Sequencing methods are also available for RNA oligonucleotides.

The present invention also contemplates derivatization or chemical modification of the subject nucleic acid fragments and oligonucleotides with chemical groups to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254: 129–132). Other ligands for cellular receptors may also have utility for improving cellular uptake, including, e.g. insulin, transferrin and others. Similarly, derivatization of oligonucleotides with poly-L-lysine can aid oligonucleotide uptake by cells (Schell, 1974, *Biochem. Biophys. Acta* 340: 323, and Lemaitre, et al., 1987, *Proc. Natl. Acad. Sci. USA* 84: 648). Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the oligonucleotides of this invention. Accordingly, the present invention contemplates derivatization of the subject oligonucleotides with groups capable of facilitating cellular uptake, including hydrocarbons and non-polar groups, cholesterol, poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids.

Derivatization of the subject nucleic acid fragments and oligonucleotides with groups that facilitate cellular uptake or target binding, can be done by any of the procedures known to one skilled in the art. Moreover, the desired groups can be added to nucleotides before synthesis of the oligonucleotide. For example, these groups can be linked to the 5-position of T or C and these modified T and C nucleotides can be used for synthesis of the present oligonucleotides. In addition, derivatization of selected nucleotides permits incorporation of the group into selected domains of the subject oligonucleotides.

In accordance with the present invention, modification in the phosphodiester backbone of the subject oligonucleotides is also contemplated. Such modifications can aid uptake of a subject oligonucleotide by cells or can extend the biological half-life of such oligonucleotides. For example, the subject oligonucleotides may penetrate the cell membrane more readily if the negative charge on the internucleotide phosphate is eliminated. This can be done by replacing the negatively charged phosphate oxygen with a methyl group, an amine or by changing the phosphodiester linkage into a phosphotriester linkage by addition of an alkyl group to the negatively charged phosphate oxygen. Alternatively, one or more of the phosphate atoms that are part of the normal phosphodiester linkage can be replaced. For example, NH—P, $CH_2$—P or S—P linkages can be formed. Accordingly, the present invention contemplates using methylphosphonates, phosphorothioates, phosphorodithioates, phosphotriesters and phosphorus-boron (Sood, et al., 1990, *J. Am. Chem. Soc.* 112: 9000) linkages. The phosphodiester group can be replaced with siloxane, carbonate, acetamidate or thioether groups. These modifications can also increase the resistance of the subject oligonucleotides to nucleases. Methods for synthesis of oligonucleotides with modified phosphodiester linkages are reviewed by Uhlmann. et al.

Additionally, different nucleotide sugars can be incorporated into the oligonucleotides of this invention. Additional binding stability can be provided by using 2'—O-methyl ribose in the present oligonucleotides. Phosphoramidite chemistry can be used to synthesize RNA oligonucleotides as described (Reese, C. B. in *Nucleic Acids and Molecular Biology*; Springer-Verlag: Berlin, 1989; Vol. 3, p. 164; and Rao, et al., 1987, *Tetrahedron Lett.* 28: 4897).

The synthesis of RNA 2'—O-methyl-oligoribonucleotides and DNA oligonucleotides differ only slightly. RNA 2'—O-methyloligonucleotides can be prepared with minor modifications of the amidite, H-phosphonate or phosphotriester methods (Shibahara, et al., 1987, *Nucleic Acids Res.* 15: 4403; Shibahara, et al., 1989, *Nucleic Acids Res.* 17: 239; Anoue, et al., 1987, *Nucleic Acids Res.* 15: 6131).

The present invention also provides methods of inhibiting cell proliferation and inducing cell death by increasing apoptosis in a cell culture. The method comprises contacting the cultured cells with an R-RNA having the sequence set forth in SEQ ID NO:2 or the cDNA having the sequence set forth in SEQ ID NO:1. Portions of the R-RNA as set forth in SEQ ID NO:2 may also be used in the method. Such RNA fragments may be obtained by in vitro transcribing the corresponding portions of the cDNA. Preferred R-RNA fragments include those having nucleotides 178–430 of SEQ ID NO:2, nucleotides 263–283 of SEQ ID NO:2, and nucleotides 374–393 of SEQ ID NO:2. Preferred cDNA fragments include those having nucleotides 178–430 of SEQ ID NO:1, nucleotides 263–283 of SEQ ID NO:1, and nucleotides 374–393 of SEQ ID NO:1. Methods of inhibiting cell proliferation and inducing cell death in a cell culture using the subject R-RNA and cDNA molecules are useful for example, in purging populations of tumor cells ex vivo. For example, such methods may be used to inhibit cell proliferation and induce cell death in bone marrow cells obtained from a patient suffering from a hematological cancer. In this embodiment, bone marrow cells are obtained from a patient suffering from a hematological cancer, the cells are contacted with an effective amount of R-RNA, R-RNA fragment, cDNA, or cDNA fragment, and after a sufficient time to allow inhibition of cell proliferation and cell death, such cells are transplanted back into the donor patient.

A further aspect of this invention provides methods for inhibiting the activation of PKR and methods for stimulating cell proliferation (expansion) in a cell culture. A method for inhibiting the activation of PKR comprises contacting the cultured cells with an effective amount of at least one of an isolated nucleic acid molecule complementary to SEQ ID NOs:1 or 2, an isolated nucleic acid molecule complementary to nucleotides 178–430 of SEQ ID NOs:1 or 2, an isolated nucleic acid molecule complementary to nucleotides 263–283 of SEQ ID NOs:1 or 2, an isolated nucleic acid molecule complementary to nucleotides 374–393 of SEQ ID NOs:1 or 2, an oligonucleotide having the sequence set forth in SEQ ID NO:6 or at least eight contiguous nucleotides of SEQ ID NO:6, an oligonucleotide having the sequence set forth in SEQ ID NO:7 or at least eight contiguous nucleotides of SEQ ID NO:7, an oligonucleotide having the sequence set forth in SEQ ID NO:8 or at least eight contiguous nucleotides of SEQ ID NO:8, an oligonucleotide having the sequence set forth in SEQ ID NO:10 or at least eight contiguous nucleotides of SEQ ID NO:10, and an oligonucleotide having the sequence set forth in SEQ ID NO:14 or at least eight contiguous nucleotides of SEQ ID NO:14.

In a preferred embodiment, a method of stimulating cell proliferation (expansion) in a cell culture comprises contacting cells of the culture with an effective amount of at least one of an oligonucleotide having the sequence set forth in SEQ ID NO:8 or SEQ ID NO:10 or at least eight contiguous nucleotides of SEQ ID NO:8 or SEQ ID NO:10.

In another aspect of the invention a method for promoting expansion of pluripotent progenitor cells is provided. The method comprises obtaining bone marrow cells from a patient and contacting said cells with an effective amount of at least one of an oligonucleotide having the sequence set forth in SEQ ID NO:10 or at least eight contiguous oligonucleotides of SEQ ID NO:10, or an oligonucleotide having the sequence set forth in SEQ ID NO:8, or at least eight contiguous oligonulceotides of SEQ ID NO:8.

The present invention also provides a method for promoting expansion of hematopoietic stem cells which comprises obtaining peripheral blood from a patient, isolating mononuclear cells and contacting said mononuclear cells with an effective amount of an oligonucleotide having the nucleotide sequence set forth in SEQ ID NO:10 or at least eight contiguous oligonucleotides of SEQ ID NO:10.

A method for promoting neutrophil expansion and development from a neutrophil depleted marrow cell culture is also provided. The method comprises obtaining marrow cells from a patient suffering from severe congenital neutropenia (SCN), contacting said cells with an effective amount of an oligonucleotide having the sequence set forth in SEQ ID NO:10 or at least eight contiguous oligonucleotides of SEQ ID NO:10, and after a sufficient time to allow neutrophil expansion, transplanting the marrow cells back into the patient.

In another aspect of the invention, there is provided a method for expansion of cells involved in wounds and burns. In this embodiment, an effective amount of at least one of the subject antisense fragments or oligonucleotides are applied directly to a wound or burn on a subject. Alternatively, an effective amount of at least one of the subject antisense fragments or oligonucleotides are admixed with a dressing and the dressing applied directly to the wound or burn.

In still another aspect of the invention, a method of expanding cells used in skin grafts is provided. The method comprises contacting epithelial cells in culture with an effective amount of at least one of the subject antisense fragments or oligonucleotides prior to using the cultured cells in a skin grafting procedure.

In yet another aspect of the present invention, there is provided a method of promoting growth and expansion of cells which are typically difficult to grow and regenerate. Such cells include nerve, muscle and brain cells. The method comprises contacting a culture of nerve, muscle, brain or any other cell type which is recalcitrant to growth and regeneration, with an effective amount of at least one of the subject antisense fragments or oligonucleotides for a sufficient time so as to stimulate cell expansion.

In another aspect of the invention, there is provided a method for preventing cell death due to apoptosis by contacting said cells with at least one of the subject isolated antisense fragments and oligonucleotides. Such a method finds particular use in expansion and maintenance of hematopoietic cell populations by minimizing programed cell death.

In still another aspect of the present invention, there is provided a method of expanding hematopoietic cells in umbilical cord blood by contacting a sample of the cord blood with at least one of the subject antisense fragments or oligonucleotides. Preferred oligonucleotides for practicing this aspect of the invention include OL-1 (SEQ ID NO:8) and OL-2 (SEQ ID NO:10).

As used herein, "cell culture" refers to any number of different vertebrate cell types which may be cultured according to methods well known to those skilled in the art. Preferred cell cultures are mammalian cell cultures. Preferred cell types for the cell cultures of the present invention include fibroblasts, bone marrow cells, mononuclear cells, neutrophils and hematopoietic stem cells. Hematopoietic stem cells include cells of erythroid lineage, granulocyte/macrophage lineage, or granulocyte/erythroid/myeloid/megakaryocyte lineage.

As used herein, "effective amount" refers to that amount which is effective in achieving the method. For example, in a method of inhibiting cell proliferation, an effective amount of R-RNA or portion of R-RNA as defined herein comprises that amount which is effective in inhibiting cell proliferation. In a method of inhibiting the activation of PKR or in stimulating cell proliferation (expansion), an effective amount of an isolated nucleic acid molecule complementary to SEQ ID NOs:1 or 2, portions thereof and oligonucleotides as defined herein, comprises that amount which is effective in inhibiting the activation of PKR or in stimulating cell proliferation. In particular, the subject oligonucleotides are added to cell cultures in an effective amount of about 0.10 $\mu$M to 100 $\mu$M final concentration, and preferably at about 1.0 to 10 $\mu$M final concentration. Nucleic acid molecules (fragments) are added to cell cultures in an effective amount of about 1 ng to about 1000 ng/ml final concentration, and preferably at about 50 ng to about 150 ng/ml final concentration.

A further aspect of this invention provides pharmaceutical compositions containing the subject nucleic acid molecules and oligonucleotides and a pharmaceutically acceptable carrier. Dosages can be readily determined by one or ordinary skill in the art based on preferred effective amounts and formulated into the subject pharmaceutical compositions.

As used herein, "pharmaceutically acceptable carrier" includes any and all solvents, dispersion media, coatings, antibacterial and antifungal agents, isotonic and absorption delaying agents, and the like that are non-toxic to the particular cells in culture. The use of such media and agents for pharmaceutical active substances is well known in the art. Except insofar as any conventional media or agent is incompatible with the either the active ingredient, i.e., the subject nucleic acid fragments or oligonucleotides or the particular cell culture type, its use in the pharmaceutical compositions is contemplated. Supplementary active ingredients can also be incorporated into the compositions.

The present invention further provides kits which comprise at least one of the subject isolated nucleic acid molecules or oligonucleotides and a pharmaceutically acceptable carrier. The pharmaceutically acceptable carrier may be packaged either separately from or admixed with the subject nucleic acid molecules and oligonucleotides.

The invention is further illustrated by the following specific examples which are not intended in any way to limit the scope of the invention.

EXAMPLE 1

ISOLATION AND ANALYSIS OF A PARTIAL cDNA ENCODING R-RNA

In order to determine the number of RNAs constituting the R-RNA activity, oligo(dT) primed cDNA synthesis using isolated R-RNA fraction as a template was carried out. Mouse 3T3-F442A cells were cultured in Dulbecco-Vogt modification of Eagle's minimal essential medium supplemented with 10% fetal calf serum and the cell extracts were prepared as previously described (Petryshyn, et al., 1984, *J. Biol. Chem.* 259:14736–14742). Cytoplasmic RNA was isolated from cultured 3T3-F442A and human CEM cells and poly(A)$^+$ and poly(A)$^-$ RNA was separated by a oligo [dT] cellulose column as previously described (Li, et al., 1991, *Eur. J. Biochem.* 195:41–48). All RNAs were dissolved in diethylpyrocarbonate treated H$_2$O (0.1%) and used immediately or stored at $-20°$ C.

R-RNA was isolated by fractionation of poly(A)$^+$ RNA on a CF-11 cellulose column as previously described (Li, et al., 1991) and used as a template for synthesis of cDNAs. cDNA synthesis was performed using the cDNA Synthesis Plus System (Amersham) according to manufacturer's instruction. RNAs were heated at 95° C. for 5 min and chilled on ice. Reverse transcription reactions (20 $\mu$l) contained 1×Taq polymerase buffer (Promega), 3.5 mM MgCl$_2$, 1 mM each dNTP, 1 unit/$\mu$ RNasin, 100 pmol oligo (dT) primer and 7.5 units AMV reverse transcriptase. The mixtures were preincubated for 10 min at 23° C., followed by incubation for 60 min at 42° C. Reactions were terminated by heating at 95° C. for 10 min. RNAs were denatured with formaldehyde (Sambrook, et al., 1989,) before use. Three distinct cDNAs were visualized after separation of reactions by electrophoresis in 1% agarose gels and autoradiography. The cDNAs were methylated and EcoRI linkers were added to the cDNAs. This procedure was followed by digestion with EcoRI as previously described (Sambrook, et al., 1989). The modified cDNAs were ligated into the vector pGEM-3Zf(−) at the $\beta$gal EcoRI site with T4 ligase. The recombinant DNAs were then used to transform *E. coli* DH-5$\alpha$ and recombinants were selected as white colonies on LB/Amp/X-gal plates. The recombinant DNAs were isolated by standard procedure (Sambrook, et al., 1989) and linearized by digestion with Sac I. The 3'-overhang created by the Sac I digestion was removed by treatment with Klenow fragment to reduce formation of artificial dsRNA during transcription (Schenborn, et al., 1985, *Nucl. Acids Res.* 13: 6223–6236). RNA transcripts were made from the linearized recombinant DNA from the T7 RNA polymerase promoter using T7 RNA polymerase (Promega) according to the manufacturer's recommended procedure. The α-globin RNA transcript was prepared from the SP6 promoter site of plasmid pHST101 (Lee Gehrke, MIT) after digestion with Bam HI. The transcripts were purified by electrophoresis on 1% agarose gels followed by electroelution of the RNA band by using a unidirectional electroelutor (IBI). Each purified RNA transcript was added at several concentrations to protein kinase assays containing latent PKR and the extent of kinase phosphorylation was determined as described in Example 2.

EXAMPLE 2

IDENTIFICATION OF R-RNA cDNA THROUGH PROTEIN KINASE ASSAYS

The gel purified transcripts of the R-RNA cDNA were treated as follows before addition to the kinase assays. For RNase T1 treatment, transcript RNA (2 µg/ml) was incubated in a mixture containing 10 unit/ml RNase T1, 30 mM Tris-HCl (pH 8.0), 300 mM NaCl, 5 mM $MgCl_2$ and 0.1 mM dithiothreitol for 15 min at 37° C. For RNase V1 treatment, transcript RNA (2 µg/ml) was incubated in a mixture containing 10 unit/ml RNase V1, 25 mM Tris-HCl (pH 7.2), 10 mM $MgCl_2$ and 200 mM NaCl for 15 min at 37° C. For heat treatment, transcript RNA (2 µg/ml) was adjusted to 150 mM KCl and heated at 100° C. for 2 min. The samples were either allowed to cool slowly to room temperature or were immediately frozen in a dry ice bath and thawed on ice. Aliquots (5 µl) were transferred to protein kinase assays to obtain a final concentration of 500 ng/ml transcript.

Protein kinase assays (20 µl) using 3T3-F442A extract (4–20 µg protein) or PKR purified from 3T3-F442A cells (0.25 µg) (Petryshyn, et al., 1983, Methods Enzymol. 9:346–362) were performed under conditions as described (Petryshyn, et al., 1984, J. Biol. Chem. 259: 14736–14742). Other additions are as indicated in FIGS. 1A and 1B. Proteins were separated by electrophoresis on 7.5% SDS-polyacrylamide gels and phosphoprotein profiles were analyzed following autoradiography (Ernst, et al., 1978, J. Biol. Chem. 253:7163–7172). Poly(I)•Poly(C) was obtained from Pharmacia and [γ-$^{32}$P] ATP (4500 Ci/mmole) was obtained from ICN.

Although a substantial number of clones were analyzed, only cDNA from one clone designated R-15 gave rise to an RNA transcript (~800 nucleotides) which facilitated the phosphorylation of a 67 KDa phosphoprotein previously identified as PKR (Petryshyn, et al., 1994, Progress in Molecular and Subcellular Biology 14:1–14; Petryshyn, et al., 1984, J. Biol. Chem. 259:14736–14742). This cDNA was termed R-RNA cDNA. The addition of this transcript to protein kinase assays containing crude 3T3-cell extract, (FIG. 1A, lanes 9 and 10) or highly purified preparations of PKR (FIG. 1B, lanes 6–8), resulted in a concentration dependent phosphorylation of PKR. In contrast, no phosphorylation of the kinase was observed in the absence of added RNA (FIG. 1A and B, Lane 1). That the observed phosphorylation of PKR was not due to either an adventitious RNA transcript or was an artifact of in vitro transcription is demonstrated by the finding that no phosphorylation of PKR was observed with identical levels of similarly prepared transcripts from all other randomly selected clones tested (four of which are shown, FIG. 1B, lanes 3–8 and lanes 11–12), or upon addition of a similarly prepared globin RNA transcript (FIG. 1B, Lanes 3–5). Moreover, addition of the RNA transcript (269 nucleotides) obtained from the pGEM vector alone was without effect.

In addition, both sense and antisense RNA probes to the R-RNA cDNA (SEQ ID NO:2 and the complementary sequence to SEQ ID NO:2, respectively) were prepared and used to address the possibility that the activation of PKR may be due to RNA:RNA hybrids formed as a result of some opposite sense strand synthesis during transcription (Schenborn, et al., 1985, Nucl. Acids Res. 13: 6223–6236). In the experiment shown in FIG. 2C (upper panel), antisense and sense RNA preparations (1,10 and 100 ng) were applied separately to nitrocellulose sheets. Because the hybridization signal using the $^{32}$P-labelled probe was sensitive to as little as 1 ng of RNA (FIG. 2C, upper panel), any contaminating opposite sense RNAs representing 1% or greater of the 100 ng sample applied would have been easily detected. The data indicated that no opposite sense RNAs could be observed in the reaction products of the R-RNA cDNA transcribed from either orientation, even after prolonged exposure of the autoradiogram. This is further supported by the finding that one of the RNA probes (sense orientation) showed no hybridization to poly(A)+ RNA which indicated a complete lack of complementary sequences, while the other probe (antisense orientation) hybridized efficiently. Furthermore, since phosphorylation of PKR was observed after addition of as little as 12.5 ng of R-RNA transcript (FIG. 1, lane 8) any contaminating RNAs representing 1% or less in amount would be insufficient to account for this level of phosphorylation.

EXAMPLE 3

R-RNA cDNA CLONE ANALYSIS AND SYNTHESIS AND PURIFICATION OF THE R-RNA TRANSCRIPT

The R-RNA cDNA (847 bp) was inserted into the vector pGEM3Zf(±) at the Eco RI site adjacent to the T7 promoter and subcloned. The orientation of the cDNA with respect to the T7 polymerase promoter was determined by restriction mapping with Hind III. As indicated in FIG. 2A, a unique Hind III site is located within the R-RNA cDNA and an additional Hind III site is located in the vector 3' to the insertion site. The DNA was separated by 1% agarose gel electrophoresis and the fragments were visualized after treatment with ethidium bromide (FIG. 2B).

After the R-RNA cDNA was subcloned into the pGEM-3Zf(−) and pGEM-3Zf(+) vectors as described above, the cDNA was sequenced in opposite directions by the dideoxy-mediated chain termination method (Sanger et al., 1977, Proc. Natl. Acad. Sci. U.S.A. 74:5463–5467) using Taq DNA polymerase (Promega). Reactions contained [α-$^{35}$S]dATP (3000 Ci/mmole, Amersham) and were carried out in the presence of the universal forward and reverse primers (18-mers) (Promega). Bidirectional nucleotide sequencing of DNA amplified by PCR was as described above except that the amplified DNA was first cloned into the pGEM vector (Promega) containing both the T7 and SP6 promoters. A sequence search of the GenBank data base using the Wisconsin Genetic Computer Group software package was conducted. The complete nucleotide sequence (847 bp) of the partial R-RNA cDNA was determined (FIG. 3A) (SEQ ID NO:1). A search of the data base revealed that this sequence had no significant homology to the human or mouse PKR cDNA. Analysis of the nucleotide sequence indicates only one possible uninterrupted open reading frame consisting of 282 amino acids (FIG. 3A), indicating the likelihood that the R-RNA is an mRNA. The R-RNA sequence deduced from the sequence of the corresponding cDNA (SEQ ID NO:1) is set forth in SEQ ID NO:2.

Figures 3B, 3C:
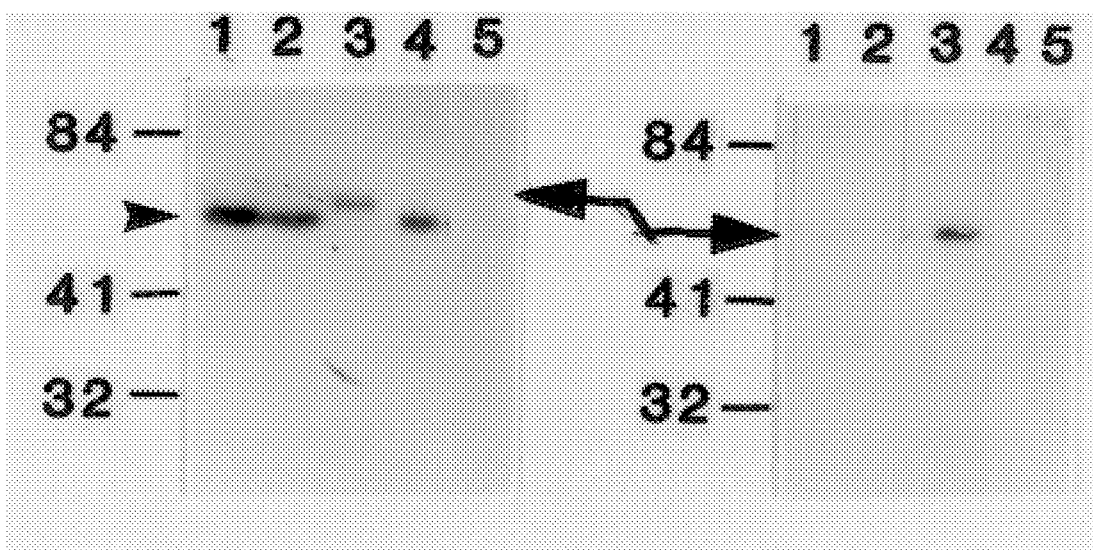
FIG. 3B is an autoradiogram of a Western blot using immune serum (1:200). Cell extracts containing 20 μg of protein were applied to each lane as follows: Lane 1, 3T3-F442A S10 extract; Lane 2, NIH-3T3 S10 extract; Lane 3, E. coli DH-5 extract; Lane 4, MG63 human osteosarcoma S10 extract; Lane 5, rabbit reticulocyte lysate (Promega). The migration position of several kaleidoscope prestained standard proteins (BIO-RAD) are indicated. Arrows indicate position of a non-specific bacterial protein antigenic to both immune and pre-immune sera. The arrowhead indicates the position of the 62 KDa protein specifically reading with the anti-peptide serum.
FIG. 3C is an autoradiogram of a Western blot using preimmune serum (1:200) with protein applied as described for FIG. 3B. The migration position of several kaleidoscope prestained standard proteins (BIO-RAD) are indicated. Arrows indicate position of a non-specific bacterial protein antigenic to both immune and pre-immune sera. The arrowhead indicates the position of the 62 KDa protein.

To examine further the possibility that the R-RNA is an mRNA, a synthetic peptide corresponding to amino acids 9-CRLVAKEYLDENNPEES-25 (SEQ ID NO:3)(FIG. 3A) was used to prepare a specific antiserum. Peptide synthesis and purification were carried out by automated FMOC solid phase synthesis as previously described (Nekhai, et al., 1996 Virology 222:193–200). Rabbit polyclonal antiserum was raised against hemocyanin-conjugated peptide (EDC Conjugation, Pierce) according to standard procedures (HRP Inc.). Preimmune serum was obtained from the same animal prior to antigen administration; western blot analysis was performed as previously described (Warrener, et al., 1991, Biochem. Biophys. Res. Commun. 180: 716–723). Western blot analysis using immune- (FIG. 3B) and preimmune- (FIG. 3C) sera indicated that a 62 KDa protein present in extracts from mouse (FIG. 3B, lane 1) and human (FIG. 3B, lane 2) 3T3 cells and from human MG63 osteosarcoma cells (FIG. 3B, lane 3), specifically reacted with antipeptide serum. This protein did not appear to be expressed in rabbit reticulocyte lysate (FIG. 3B, lane 5) or in extracts from E.coli (FIG. 3B, lane 4). Since the 62 KDa protein was detected in at least 3 of the 4 eukaryotic cell extracts but not in a prokaryotic cell, it suggests that the R-RNA encoding the 62 KDa protein is a widely expressed eukaryotic mRNA. The function of the protein is unknown. Recently, two sequences have been identified as human sequences with near perfect nucleotide identity to the R-RNA sequence of the present invention. The two sequences are an EST-cDNA sequence from infant brain which is 99% identical over its entire 362 bp stretch (Khan, et al., 1992, Nature. Genet. 2: 180–85) and an cDNA which is 100% identical over a 231 bp overlap with the R-RNA sequence (Obradobic et al., EMBL Accession No. HO4703). The evolutionary significance of the high level of nucleotide conservation remains to be elucidated but may be explained by a requirement for the R-RNA to encode a functional protein and also to retain an ability to form a specific structure(s) necessary for the activation of PKR.

The R-RNA transcript was transcribed in vitro from the recombinant pGEM-3zf(±) plasmid after linearization with Sma 1 (Promega). Transcription from the T7 promoter was carried out using the MegAscript kit (Ambion) according to the manufacturer's instructions. The reaction mix was separated by electrophoresis on 0.75 mm, 4% acrylamide/bisacrylamide (19:1) TBE gels, containing 7M urea. The quantity of the RNA synthesized allowed visualization of bands using shadow-casting. The advantage of this method is that ethidium bromide, which may interfere with kinase assays can be avoided. The gel was covered in plastic wrap and placed on top of an intensifying screen (Kodak). The gel was exposed to short wave UV light (254 nm). The shadow cast by the RNA was clearly visible. Gel slices containing the discrete 847 nt R-RNA transcript were excised, and the RNA eluted overnight in a solution (300 µl) containing 2M $CH_3COONH_4$, 0.1% SDS and 0.5 mM EDTA. The RNA was precipitated in ethanol, resuspended in DEPC-treated $H_2O$ and stored under liquid nitrogen. The gel purified R-RNA transcript was digested with RNAse T1 (Pharmacia) and RNAse V1 (Pharmacia) and utilized for protein kinase reactions.

EXAMPLE 4

PCR ANALYSIS

PCR analysis was performed utilizing DNA from several eukaryotic sources as a template and the specific primer pair designed to amplify a 380 bp region of the R-RNA cDNA fragment. The oligonucleotide primer pairs were selected from the sequence of R-RNA cDNA (see FIG. 3). The upstream primer corresponding to nucleotides 132–151 (5'-GAAAGTGTAGGCTTGTCGCA-3') (SEQ ID NO:4) and downstream primer corresponding to nucleotides 492–511 (5'-CAGCATTAGGAGTTGTGCCC-3') (SEQ ID NO:5) were synthesized using a Model 391 DNA synthesizer (Applied Biosystem) according to the manufacturer's instructions. PCR reactions were carried out as previously described, (Kawasaki, E. S. 1990 in M. A Innis, D. H Gelfand, J. J. Sninsky, and T. J. White, (eds) PCR Protocols: a Guide to Methods and Applications, pp. 21–27, Academic Press, New York) with some modifications. The reactions were adjusted to contain in a final volume of 50 µl: 1×Taq polymerase buffer, 3.5 mM $MgCl_2$, 1.25 unit of Taq polymerase (Promega) and 25 pmol of primer pairs. Amplification was carried out using a Biosycler Oven (BIOS Corp.) for 35 cycles under the following conditions: denaturation was for 20 sec at 92° C., synthesis was for 20 sec at 72° C., and annealing (20 sec) was carried out sequentially for 2 cycles at 72° C., 70° C., 68° C., 66° C., 64° C., 61° C., 58° C. and 21 cycles at 55° C. Aliquots (20 µl) from each sample were separated by electrophoresis on 1% agarose gels containing 0.045 M Tris-borate and 0.001 M EDTA, and visualized after staining with ethidium bromide.

Figure 4A:
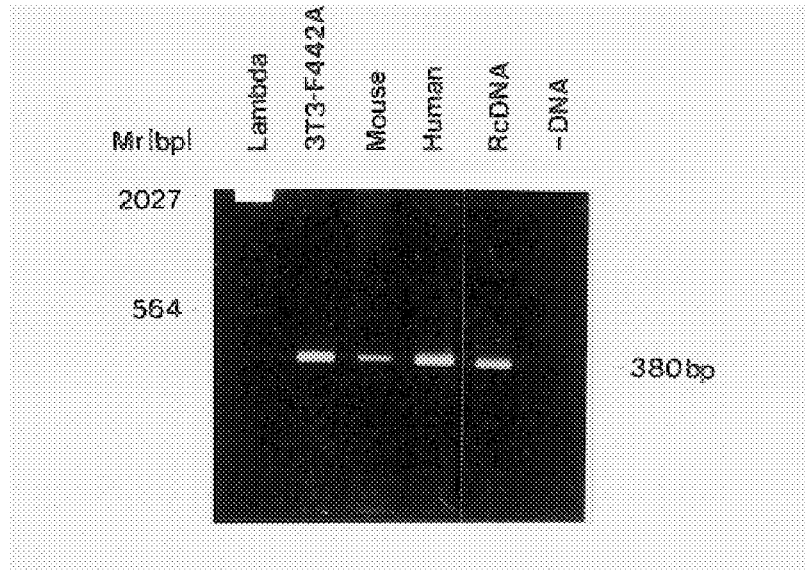
FIG. 4A is an ethidium bromide stained electrophoretic gel depicting the distribution of the R-RNA DNA sequence. PCR amplified template genomic DNA (1 μg), from mouse 3T3-F442A, mouse liver tissue, human CEM, and yeast cells were loaded as indicated. The migration position of several fragments of Hind III digested lambda DNA is shown on the left.
Figure 4B:
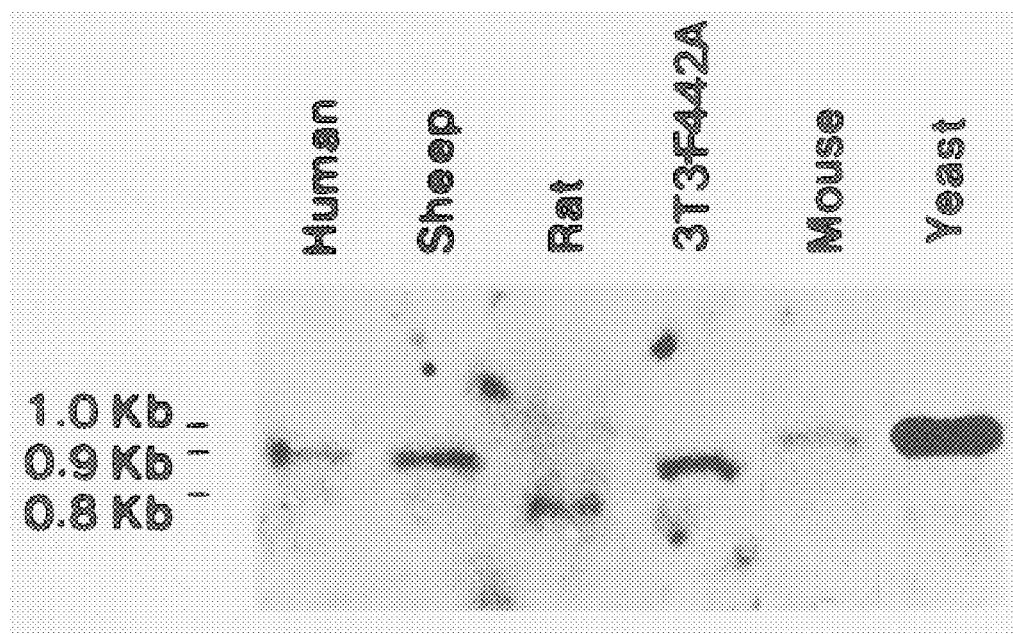
FIG. 4B is an autoradiogram of a southern blot. The agarose gel was loaded with EcoRI digested genomic DNA (30 ug) prepared from human CEM cells, sheep liver tissue, rat liver tissue, mouse 3T3-F442A cells, mouse liver tissue, and from yeast as indicated. The blot was hybridized to $^{32}$P-labeled R-RNA partial cDNA ($1.3 \times 10^9$ cpm/μg, $1 \times 10^7$ cpm/ml) and exposed for two weeks at $-76°$ C. with an intensifying screen. The approximate size of the hybridizing bands is shown on the left and was determined from the migration position of Hae III digested Phi ×174 DNA.

The results shown in FIG. 4A indicate that genomic DNA from mouse 3T3-F442A and human CEM cells, and DNA from mouse liver served as a template to amplify a 380 bp region of the R-RNA cDNA fragment. Moreover, a 380 bp region was also amplified when yeast DNA was used as a template for amplification (FIG. 4A). In addition, each of the amplified DNAs were sequenced and found to be identical to the original R-RNA cDNA with the exception of a single reproducible nucleotide change in the human CEM cell amplified DNA sequence. To rule out the possibility that contaminating DNA was amplified during the PCR analysis, genomic DNA from liver tissue of sheep, rat and mouse and from human CEM, 3T3-F442A and yeast cells was digested with Eco RI and subjected to direct Southern blot analysis using the R-RNA cDNA probe. The data clearly indicate that the R-RNA cDNA probe hybridized to one prominent band present in the digested DNA from each of these sources (FIG. 4B). The relative size of the hybridizing fragments was approximately the same for each of the digested DNA samples examined except for that of the rat which was diminished. It is likely that the rat sequence is less conserved and this is reflected in an altered EcoRI site. In contrast, multiple restriction bands were detected in genomic DNA from human, mouse and yeast cells following digestion with BamHI or SmaI. These findings indicate that the R-RNA cDNA sequence is present in eukaryotes, and that a portion of the sequence is highly conserved in nature. This is further confirmed by two independent reports describing short human cDNA sequences with essentially 100% nucleotide identity to the R-RNA sequence over the region where sequence information was available. (EMBL accession number X55722; Khan, et al., 1992, Nature Genet. 2: 180–85).

EXAMPLE 5

Figure 2C:
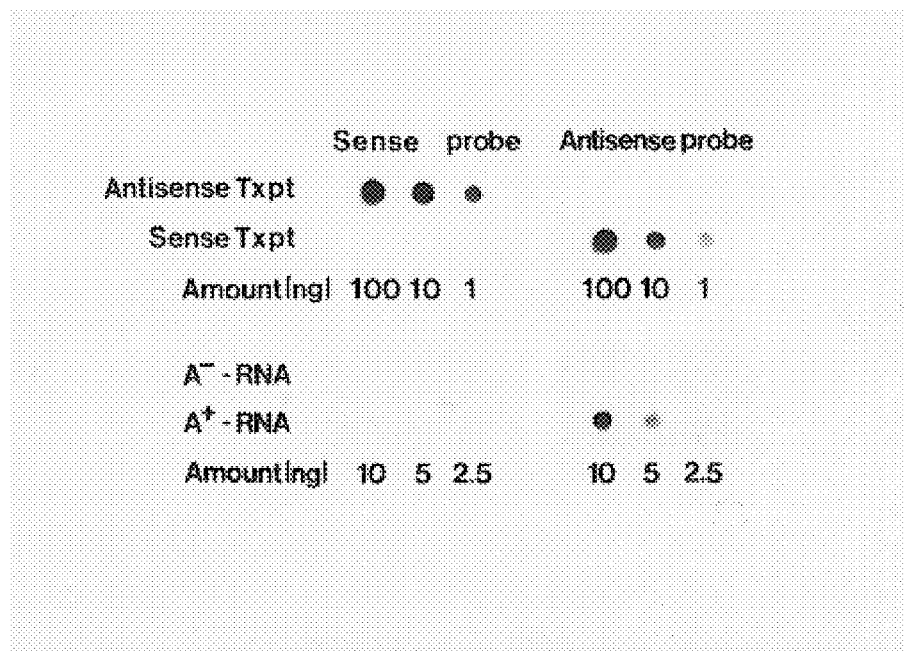
FIG. 2C is an autoradiogram of a dot blot where poly(A)+ and (A)– RNA prepared from confluent cultures of 3T3-F442A cells were applied to two separate nitrocellulose sheets in the amounts indicated followed by separate hybridization with the 32P-labeled antisense or sense transcript.

NORTHERN AND DOT BLOT ANALYSIS $^{32}P$ labeled and non-radioactive RNA transcripts were prepared from each construct using T7 polymerase after linearization with BamHI. RNAs were denatured with formaldehyde (Sambrook, et al., 1989) before use. For Northern blots, the RNAs were separated by electrophoresis on a 1% agarose-formaldehyde gel and transferred to nitrocellulose paper (Schleicher & Schuell) as described (Sambrook, et al., 1989). For dot blots, the RNAs were diluted as indicated in FIG. 2C and applied onto nitrocellulose under vacuum. Both blots were prehybridized for 4 h at 42° C. in a solution containing 5×SSPE, 50% (v/v) formamide, 5×Denhardt's solution and 10% (w/v) dextran sulfate. Hybridization was for 18 h at 42° C. in the same solution containing denatured salmon sperm DNA (20 μg/ml) and [α-$^{32}$P]dCTP-labeled R-RNA cDNA probe (25 ng/ml) prepared by nick translation ($10^{7-108}$ cpm/μg) for Northern blots (Sambrook et al., 1989) and [α-$^{32}$P]ATP-labeled R-RNA transcripts ($10^7$ cpm/μg) for dot blots (1×$10^6$ cpm/ml hybridization buffer). An actin DNA probe of similar size and labeled to the same specific activity as the R-RNA cDNA probe was used in some experiments in order to compare the relative amounts of the hybridization signal between the R-RNA and actin RNA observed in the total cytoplasmic RNA preparation. Following hybridization, the blots were washed 4 times with a solution containing 2×SSC and 0.1% SDS for 5 min each at room temperature. This was followed by 2 washes with 0.1×SSC and 0.1% SDS at 60° C. Blots were air dried and subjected to autoradiography.

Figure 5A:
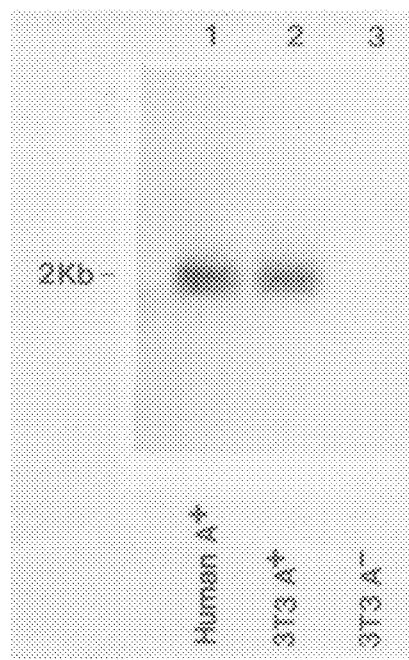
FIG. 5A is a Northern blot analysis of the R-RNA. Cellular RNAs were separated on a 1% formaldehyde denaturing agarose gel and transferred to nitrocellulose paper. The blot was hybridized to $^{32}$P-labeled R-RNA partial cDNA ($4.5 \times 10^8$ cpm/μg, $1 \times 10^6$ cpm/ml of hybridization buffer). The gel was loaded as follows: Lane 1, 30 μg of human CEM cell poly (A)$^+$ RNA (Human A$^+$); Lane 2, 30 μg of 3T3-F442A cell poly(A)$^+$ RNA (3T3 A$^+$) and Lane 3, 30 μg of 3T3-F442A cell-poly (A)$^-$ RNA (3T3 A$^-$).
Figure 5B:
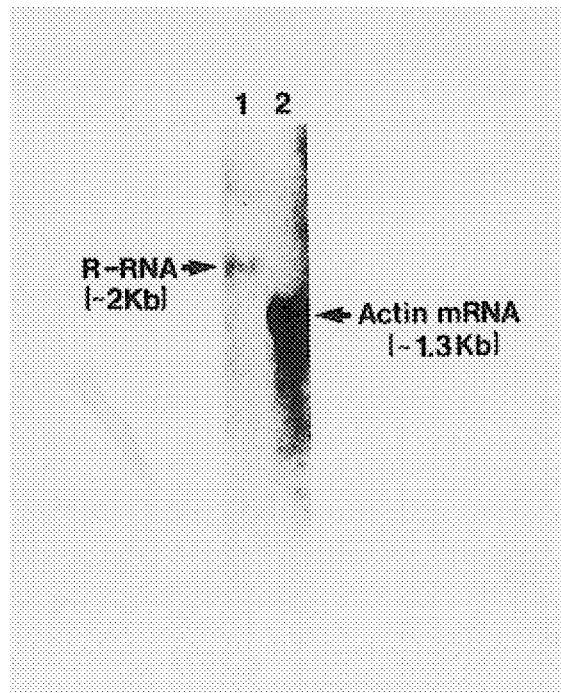
FIG. 5B is a Northern blot analysis of total cytoplasmic RNA (40 μg) prepared from 3T3-F442A cells. The probes used for hybridization were as follows: Lane 1, 0.7 μg R-RNA cDNA probe ($1 \times 10^8$ cpm/μg), Lane 2, 0.3 μg actin DNA probe (0.7 Kb, $1 \times 10^8$ cpm/μg)

Previous studies have demonstrated that the R-RNA activity initially observed in the total cytoplasmic RNA obtained from confluent cultures of 3T3-F442A cells quantitatively co-purified with the poly(A)$^+$ RNA after separation on oligo(dT)-cellulose (Li, et al., 1991, *Eur. J. Biochem.* 195: 41–48). Consistent with this finding are the results of Northern blot analysis which demonstrate that the R-RNA cDNA hybridizes to a distinct RNA of approximately 2 Kb in size present in the poly(A)$^+$ RNA (FIG. 5A, Lane 2) and the total cytoplasmic RNA (FIG. 5B, Lane 1), but not in the poly(A)$^-$ RNA prepared from 3T3-F442A cells (FIG. 5A, Lane 3; FIG. 2C). Northern blot analysis also indicates that the hybridizing cytoplasmic RNA is of low abundance (relative to actin mRNA) as would be expected for an RNA involved in PKR activation (FIG. 5B, compare Lanes 1 and 2). These data further indicate that the R-RNA cDNA is not full-length and accounts for only about 48% of the R-RNA sequence. Of additional interest was the observation that the R-RNA cDNA probe hybridized to an RNA of approximately 2 Kb in size, present in the poly (A)$^+$ RNA fraction prepared from human CEM cells (FIG. 5A, Lane 1). This indicates that the R-RNA is expressed in some human cells and that it has a functional role in cells other than 3T3-F442A mouse fibroblasts.

EXAMPLE 6

EFFECT OF DNA/RNA HYBRIDIZATION ON THE PHOSPHORYLATION OF PKR

In order to address the possibility that the screening procedure used to isolate the R-RNA cDNA and identify the R-RNA could have missed some other activating RNAs, hybridization experiments were performed. Complementary base pairing between the R-RNA cDNA and the R-RNA would specifically disrupt the secondary structure in the R-RNA which interacts with PKR, but would have no effect on other potentially PKR activating RNAs which would remain active.

To carry out DNA/RNA hybridizations, the cytoplasmic RNA (2 μg), the isolated R-RNA (200 ng) and the R-RNA transcript (20 ng) were each mixed with a 5-fold excess (wt/wt) of gel purified R-RNA cDNA and heated at 95° C. for 5 min in the presence of 100 mM KCl. The mixtures were then allowed to cool slowly to room temperature. For controls, parallel hybridization reactions were performed containing: 100 mM KCl only; the RNAs alone; cDNA alone; poly(I)•poly(C) alone; and poly(I)•poly(C) with 5-fold excess cDNA. Aliquots (5 μl) were added to protein kinase assays.

Figure 6:
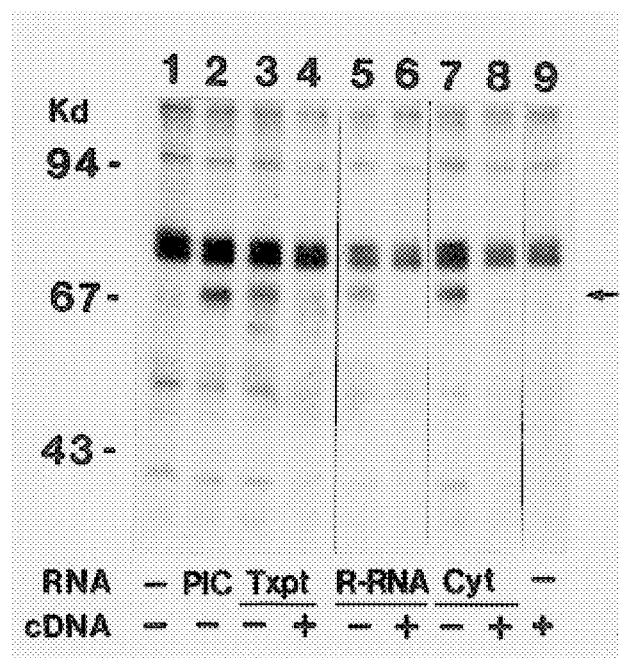
FIG. 6 is an autoradiogram of a southern lot which demonstrates the effect of the R-RNA cDNA on R-RNA activity. DNA/RNA hybridization reactions (10 μl) containing the R-RNA transcript (20 ng) (Txpt), the isolated R-RNA (100 ng) and the total cytoplasmic RNA fraction (2 μg) (Cyt) were carried out in the presence and absence of 5-fold excess gel purified R-RNA cDNA . Aliquots (5 μl) were added to protein kinase assays containing 3T3-F442A cell extract as indicated in the figure. Other additions contained hybridization buffer (Lane 1); hybridization buffer and 150 ng/ml poly(I)•poly(C) (PIC) (Lane 2) and hybridization buffer and 250 μg/ml R-RNA cDNA (Lane 9).

The data in FIG. 6 demonstrate that under the hybridization conditions used, the R-RNA cDNA efficiently prevented the phosphorylation of PKR by the R-RNA transcript (FIG. 6, Compare Lanes 3 and 4). The R-RNA cDNA alone did not cause phosphorylation of the kinase (FIG. 6, Lane 9) or affect the level of its phosphorylation by low levels of poly(I)•poly(C) (data not shown). Of particular importance is the finding that the R-RNA cDNA completely prevented the R-RNA activity in the isolated R-RNA (FIG. 6, Compare Lanes 5 and 6), and in the total cytoplasmic RNA preparation (FIG. 6, Compare Lanes 7 and 8). Moreover, the addition of several unrelated DNAs including the PGEM vector DNA to hybridization reactions had no effect on the subsequent level of PKR phosphorylation by these activating RNA preparations (data not shown). This data indicates that a single cellular RNA is largely responsible for the phosphorylation and activation of PKR.

EXAMPLE 7

PROPERTIES OF THE R-RNA TRANSCRIPT

Figure 7:
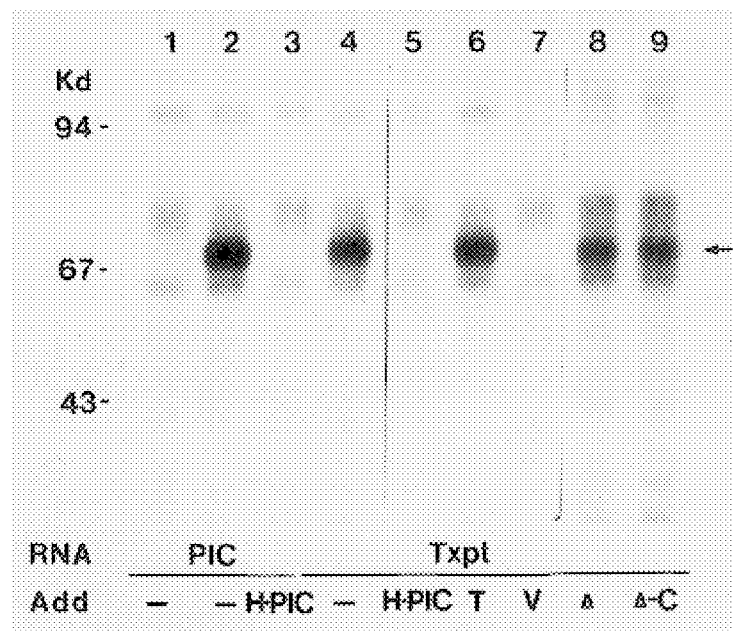
FIG. 7 is an autoradiogram of an agarose gel run with samples of the protein kinase assay with added R-RNA transcript. High levels of poly(I)•poly(C) (50 μg/ml) were added to some assays as indicated prior to incubation. Assays contained the following additions. Lane 1, no RNA; Lane 2 and 3, 150 ng/ml poly(I)•poly(C) (PIC); Lanes 4–9 contained R-RNA transcript (Txpt) that has been treated as follows: Lane 4 and 5, no treatment; Lanes 6, RNase T1 (T); Lane 7, RNase V1 (V), Lane 8, 100 C for 2 min and slow cooled (Δ); Lane 9, 100 for 2 min and rapidly cooled (Δ-C); High concentrations of poly(I)•poly(C) (H•PIC) were added to assay indicated in Lanes 3 and 5.

A distinct feature of PKR is that low levels of dsRNA are required for its phosphorylation and 5 activation, but high levels of dsRNA prevent phosphorylation and activation (Farrell et al., 1977, *Cell* 11: 187–200; Petryshyn et al., 1975 *J. Biol. Chem.* 250: 409–417). Protein kinase assays were performed in order to determine if high concentrations of poly(I)•poly(C) could also prevent the phosphorylation of PKR by the R-RNA transcript. The assays were performed under the conditions described in Example 2. Addition of the R-RNA transcript (2.5 μg/ml) to protein kinase assays resulted in a level of PKR phosphorylation (FIG. 7, Lane 4) similar to that observed with poly(I)*poly(C) (150 ng/ml) (FIG. 7, Lane 2). This phosphorylation was completely prevented by addition of high concentrations (50 μg/ml) of poly(I)•poly(C) (FIG. 7, Lanes 3 and 5). These results demonstrate that the R-RNA transcript facilitates PKR phosphorylation in a manner similar to that observed with low levels of viral and synthetic dsRNA (Petryshyn et al., 1984, *J. Biol. Chem.* 259: 1436–14742; Petryshyn et al., 1988, *Proc. Natl. Acad. Sci. USA* 85: 1427–1931; Galabru et al., 1989, *Eur. J. Biochem.* 178:581–589; Edery et al., 1989, *Cell* 56: 303–312; Petryshyn et al., 1975; Bischoff et al., 1989, *Virology* 172:106–115). Moreover, while maximal phosphorylation was observed with concentrations of between 0.5–2.5 μg/ml of added R-RNA transcript, concentrations at 10 μg/ml and above resulted in a concentration dependent prevention of PKR phosphorylation. Thus the transcript also elicits a paradoxic pattern of PKR phosphorylation similar to that observed with those viral and synthetic dsRNAs which activate PKR. To partially characterize the structural features in the R-RNA transcript involved in PKR activation, the R-RNA transcript was subjected to digestion with the ssRNA-specific RNase T1 and the dsRNA-specific RNase V1, and to thermal denaturation. The activity of the transcript was completely abolished by treatment with RNase V1 (FIG. 7, Lane 7) while RNase T1 had no effect on its activity (FIG. 7, Lane 6). Thermal denaturation (100° C. for 2 min) of the transcript followed by either slow cooling (FIG. 7, Lane 8) or rapid cooling (FIG. 7, Lane 9) prior to addition to protein kinase assays had no effect on the activity of the transcript. These results indicate that the R-RNA transcript contains one or more dsRNA regions which are necessary for the phosphorylation of PKR. This region(s)

appears to be a favorable structure(s) which reanneals following thermal denaturation to retain sufficient dsRNA structure to facilitate PKR phosphorylation. Moreover, these observed effects of heating, high concentrations of poly(I)•poly(C) and RNases T1 and V1 on the activity of the R-RNA transcript are essentially identical to those previously reported using the R-RNA fraction isolated from the total cytoplasmic RNA of 3T3-F442A cells (Li et al., 1991 Eur. J. Biochem. 195:41–48). Thus it is likely that the transcript, although shorter in length than the isolated R-RNA, retains the same structural features involved in the activation if PKR.

EXAMPLE 8

ASSOCIATION OF THE R-RNA WITH PKR

In order to determine whether the R-RNA was specifically associated with PKR that had been directly isolated from 3T3-F442A cells, PKR was immune precipitated from cell extracts using anti-PKR antibodies. The RNA in the immune complex was isolated and subjected to reverse transcriptase dependent PCR (RT-PCR) analysis. An association would be expected under physiologic conditions where these cells exhibited high levels of kinase activation (Petryshyn, et al., 1984, J. Biol. Chem. 259: 14736–14742; Petryshyn, et al., 1988, Proc. Natl. Acad. Sci. U.S.A. 85: 1427–1431). It has previously been shown that under these conditions, the kinase was specifically and quantitatively precipitated (Petryshyn, et al., 1988) and that RNA(s) containing the R-RNA activity was specifically associated with PKR in the immune complex (Li, et al., 1991, Eur. Bio. Chem. 195 41–48).

3T3-F442A cell extract (2.4–4.2 mg protein) was incubated with 200 μl of rabbit anti-3T3-PKR serum (Petryshyn, et al., 1984) on ice for 1 h. The mixture was transferred to a tube containing a 200 μl pellet of protein A-Sepharose which had been previously washed 3 times with TBS buffer (10 mM Tris-HCl (pH 7.4), 50 mM NaCl, 1 mM phenylmethylsulfonyl fluoride, 100 kU/ml aprotinin, and 0.1% Triton x-100) and incubated overnight at 4° C. with constant shaking. The mixture was then centrifuged for 1 min in a macrophage to collect the precipitate which contained the complex of PKR and the associated R-RNA. The precipitate was washed 3 times with 500 μl TBS buffer and resuspended in 500 μl TBS buffer. The R-RNA was extracted from the complex with phenol:chloroform (1:1) followed by an extraction with chloroform. The R-RNA was precipitated with ethanol and resuspended in 20 μl H$_2$O.

RT-PCR analysis was performed as previously described (Kawasaki, E. S., 1990) with some modifications RNAs were heated at 95° C. for 5 minutes and chilled on ice. Reverse transcription reactions (20 μl) contained 1×Taq polymerase buffer (Promega), 3.5 mM MgCl$_2$, 1 mM each of dNTP, 1 unit/μl RNasin, 100 pmol oligo (dt) primer and 7.5 units AMV reverse transcriptase. The mixtures were preincubated for 10 minutes at 23° C., followed by incubation for 60 minutes at 42° C. Reactions were terminated by heating at 95° C. for 10 minutes.

Figure 8:
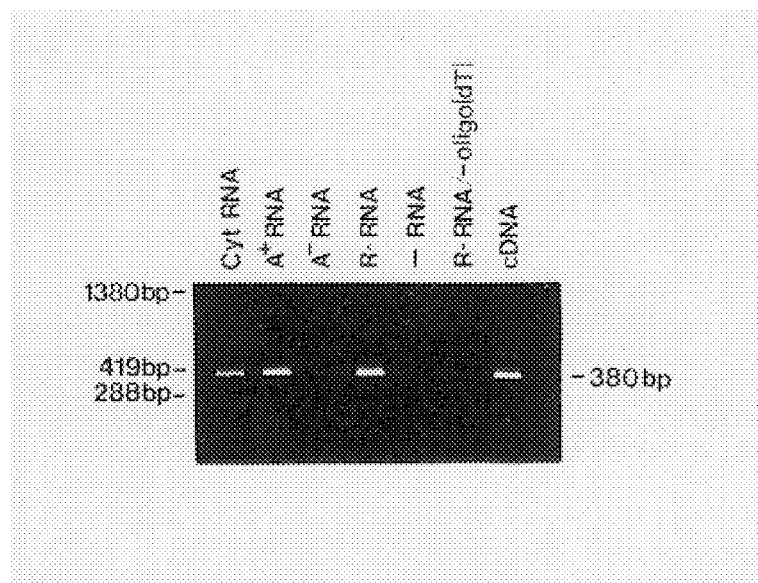
FIG. 8 is a photograph of an ethidium bromide stained gel after electrophoresis of PCR reactions and demonstrates the association of the R-RNA with PKR. Total cytoplasmic RNA (Cyt RNA, 2 μg); poly (A)$^+$ RNA (A$^+$ RNA, 0.4 μg); poly (A)$^-$ RNA (A$^-$, RNA, 0.4 μg) and extracted RNA (R-RNA, 0.3 μg) were added to reactions as indicated. Control assays containing no added RNA (–RNA) or no oligo (dT) primer (R-RNA—oligo (dT)) were performed as indicated. In one assay direct PCR was carried out using the R-RNA cDNA (cDNA, 1.0 ng) as a template. The migration position of several fragments of Hpa I digested T7 DNA is shown on the left.

The results shown in FIG. 8 indicate that RT-PCR reactions containing total cytoplasmic (FIG. 8, Lane 1) or poly (A)$^+$ RNA (FIG. 8, lane 2) gave rise to a single amplified product of approximately 380 bp. This is the size of the amplified DNA expected from reactions using this specific primer pair, and was also observed by direct PCR of the R-RNA cDNA (FIG. 8, Lane 7). Importantly, the putative R-RNA extracted from immune precipitates containing PKR, gave rise to a single amplified DNA of the expected size (FIG. 8, Lane 4). RT-dependent amplification was not observed in reactions which contained no RNA (FIG. 8, Lane 6) or when the oligo(dT) primer was omitted (FIG. 8, Lane 5). As expected, no amplification was observed when the A$^-$ RNA fraction was used as a template in the RT-PCR reaction (FIG. 8, Lane 3). In addition, direct dot blot analysis of the RNA extracted from immune precipitates containing PKR also revealed specific hydridization to the R-RNA cDNA probe (data not shown). While the possibility cannot be excluded that other non-activating RNAs may have non-specifically co-precipitated with PKR, the results demonstrate that the R-RNA is associated with the kinase that had been directly obtained from 3T3-F442A cells. Furthermore, the association of the R-RNA with PKR in cell extracts makes it highly unlikely that its activation by the isolated or transcript R-RNA (FIGS. 1 and 6) is due to artifactual RNA created by isolation or synthesis procedures. This finding demonstrates a physiologic role for the R-RNA in the activation of PKR.

EXAMPLE 9

ANALYSIS OF THE DOUBLE-STRANDED CONTENT OF THE R-RNA

Previous studies have shown that activation of PKR by cytoplasmic RNA obtained from 3T3-F442A cells or by the R-RNA transcript obtained from 3T3-F442A cell cDNA is dependent on single-stranded (ss)-RNA containing double-stranded (ds)-structure(Li, et al., 1991, Eur. Bio. Chem. 195: 41–48 and Li, et al., 1997, Mol. Cell. Diff. (In Press)). To determine the relative extent of ds-structure in the R-RNA transcript involved in activation of PKR, its activity was examined via protein kinase assays over a broad concentration range and compared to activation with poly(I)-poly(C).

Figure 9:
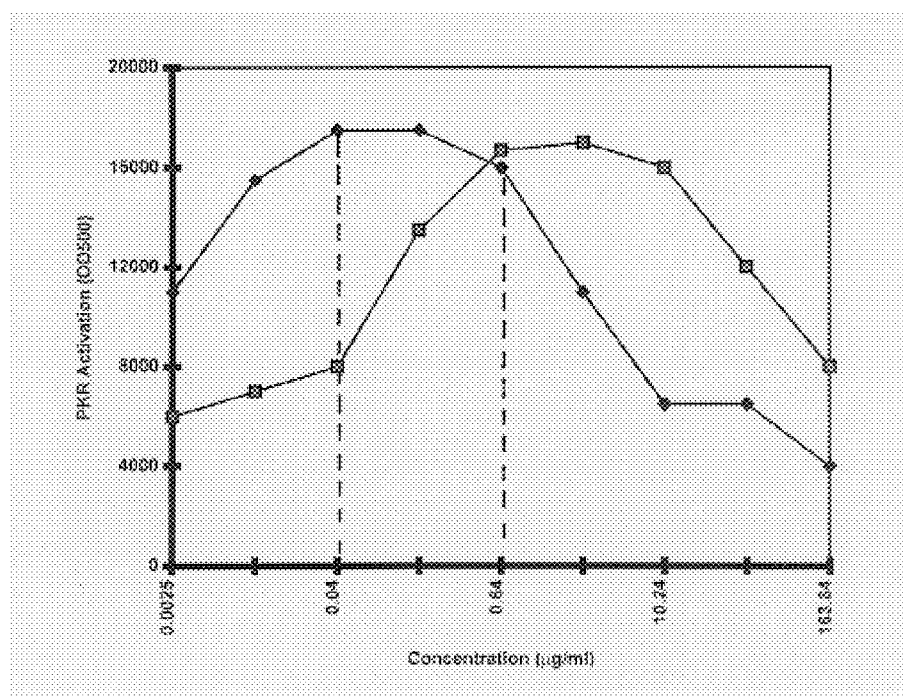
FIG. 9 graphically depicts a comparison between Poly(I)-Poly(C) and R-RNA in the autophosphorylation of PKR. Poly(I)-poly(C) and the R-RNA transcript were added to protein kinase assays at the final concentrations indicated in the figure. The extent of phosphorylation of PKR was determined by scanning densitometry (OD 500 nm) of autoradiograms. Solid diamonds represent Poly(I)-poly(C). Open squares represent R-RNA.

Protein kinase assays (20 μl) using PKR purified from rabbit reticulocytes (0.5 ng)(Petryshyn, et al., 1983, Methods Enzymol. 99: 346–362) were performed under conditions as described (Petryshyn, et al., 1988, Proc. Natl. Acad. Sci. U.S.A. 85: 1427–1431). Other additions are as indicated in FIG. 9. Proteins were separately by electrophoresis on 7.5% SDS-polyacrylamide gels (SDS-PAGE) and phosphoprotein profiles were analyzed following autoradiography. Poly(I)-poly(C) was obtained from Pharmacia and [γ-$^{32}$P]ATP(4500 Ci/mmol) was obtained from Dupont. The extend of PKR phosphorylation was quantitated from autoradiograms by scanning densitometry (Shimadzu, Kyoto, Japan).

Figures 10A, 10B:
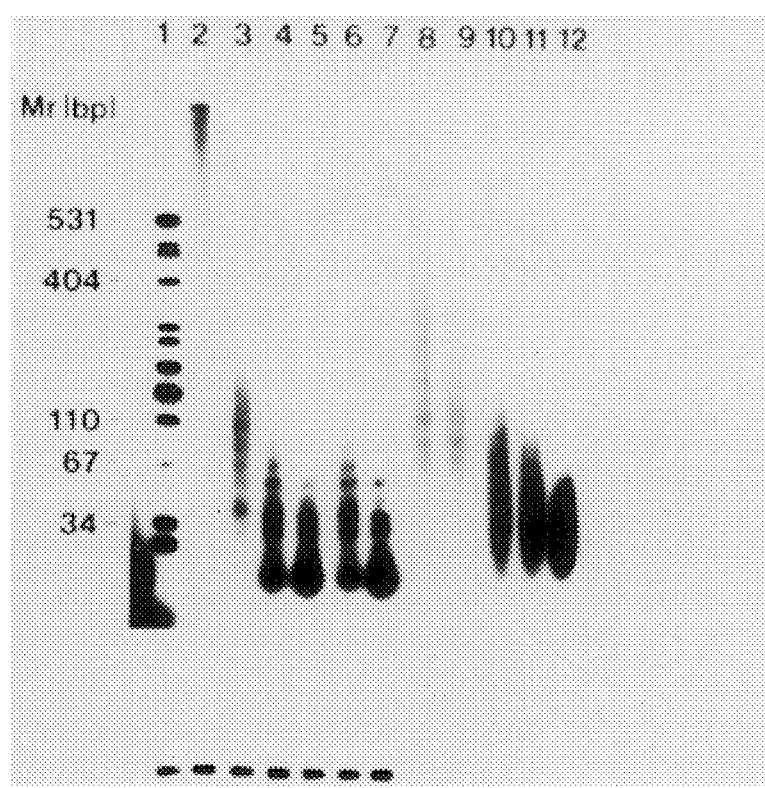
FIG. 10A is an autoradiogram demonstrating the Effect of RNase Digestion on the Activity of the R-RNA Transcript. After radiolabeled or unlabeled R-RNA transcript was digested with either RNase T1 or RNase VI, digestion reactions using radiolabeled transcript were subjected to electrophoresis on 5% polyacrylamide gels. Lane 1, Radiolabeled pGEM-3zf(–) digested with Hpa II; lane 2, R-RNA transcript without RNase digestion; lane 3–6, digestion with RNase T1 at a final activity of 0.78, 1.56, 3.13, and 12.5 units/ml respectively; lanes 7–11, digestion with RNase VI at a final activity of 0.05, 0.10, 0.19, 039 and 0.78 units/ml respectively. The figure is an autoradiogram.
FIG. 10B is an autoradiogram of a gel loaded with the digestion reactions of FIG. 10A added to protein kinase containing purified PKR. Lane 1, no added RNA; lane 2, 150 ng/ml poly(I)-poly(C); lanes 3–7, RNase T1 digestion reactions (2–6); lanes 8–12, RNase VI digestion reactions (7–11). The final activity of the RNases in the digestion reactions was the same as in FIG. 10A.

The R-RNA transcript and poly(I)-poly(C) were added to the protein kinase assays at the final concentrations indicated in FIG. 9, and the extent of activation was determined by quantitation of the level of PKR phosphorylation. The results show that the profile of activation observed with the R-RNA transcript was similar to that observed with poly(I)-poly(C)(FIG. 9). Both RNAs show a transient effect on PKR, i.e., a dose dependent activation at low concentration followed by a dose dependent inhibition of activation at higher concentrations. The transient effect of poly(I)-poly (C) observed is consistent with previous reports (Farrell et al., 1977 Cell 11: 187–200; Hunter et al., 1975, J. Biol. Chem. 250: 409–417). However, the minimum concentration of the R-RNA transcript (0.64 ug/ml, dashed line, FIG. 9), necessary for optimal activation of PKR is 16-fold higher than the minimal concentration of poly(I)-poly(C) required for a similar level of activation, (0.04 ug/ml, dashed line, FIG. 9). Since poly(I)-poly(C) can be assumed to be entirely composed of ds-structure (Hunter, et al., 1975, J. Bio. Chem. 250: 409–417), and the R-RNA transcript contain both ssand ds-structures (Li, et al., 1997, *Mol. Cell. Diff.* (In Press)), the difference in the relative minimum concentrations needed for optimal activation may represent differences in the extent of ds-structure between the two molecules. This implies that the ds-region involved in activation of PKR constitutes a small portion of the secondary structure with the R-RNA. This is further supported by the observation that digestion of the transcript with ss-RNA specific RNase Ti resulted in formation of RNA fragments of approximately 60 bp or less in length (FIG. 10A, lanes 3–7). These fragments are still capable of activating PKR (FIG. 10B, lanes 3–7) indicating that they retain the critical ds-structure(s) even after digestion with high levels of RNase T1. Digestion with ds-RNA specific RNase VI however, results in formation of fragments of a larger average size (FIG. 10A, lanes 8–12) that are unable to facilitate activation of PKR (FIG. 10B, lanes 8–12).

EXAMPLE 10

MAPPING OF SECONDARY-STRUCTURE INVOLVED IN ACTIVATING PKR

To delineate the location of the region of secondary structure and nucleotide sequence of R-RNA involved in activation of PKR, RNA:DNA hybridization reactions were carried out utilizing the R-RNA transcript and specific restriction fragments from its cDNA. The mappings of the secondary-structure within the R-RNA important for activation of PKR can be established by determining which of the known restriction fragments interfere with the capacity of the R-RNA to activate PKR. This is because such RNA:DNA duplexes are stable once they form, and they disrupt the natural secondary-structure of the R-RNA. Digestion with Alu I was selected because such digestion gave rise to five asymmetric fragments which could be conveniently separated and four of the fragments were easily purified.

FIG. 11A is a schematic representation indicating the known restriction map of the 847 bp R-RNA cDNA and the orientation for the five predicted Alu I fragments. Following digestion with Alu I, the predicted 284, 226, 178 and 133 bp fragments were obtained and highly purified by gel electrophoresis.

To prepare highly purified R-RNA cDNA insert, isolated pGEM-3zf(±) recombinant plasmid was digested with EcoR1 (Li et al., 1997, *Mol. Cell. Diff.* (In press.)) and R-RNA cDNA (1 mg) insert was separated by electrophoresis on 1.2% low melting temperature agarose (NuSieve, FMC Bioproducts). The 847 bp R-RNA cDNA was purified from gel slices using the QIAEXII, extraction kit (Qiagen). The purified cDNA was digested at 37° C. with Alu I(NEB). The reaction productions were separated by electrophoresis on 1.5% agarose gels and the expected 284, 226, 173 and 133 bp fragments were individually purified as described above. The expected 26 bp fragment was not recovered. The purified cDNA fragments were resuspended in DEPC-treated $H_2O$ and stored at -20° C. at a concentration of 20–25 ug/ml.

Figure 11C:
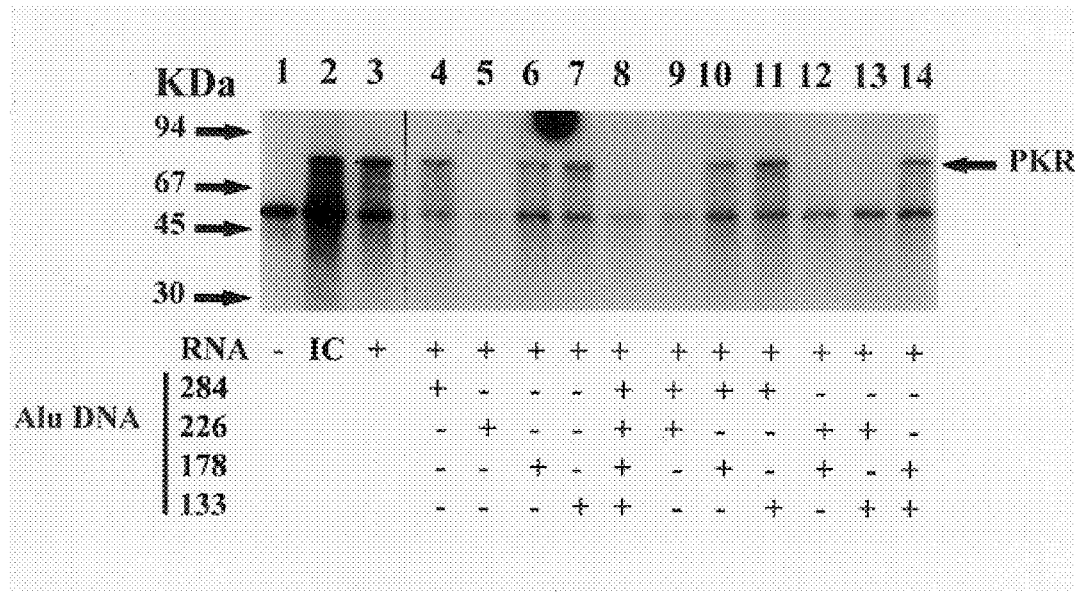
FIG. 11C is an autoradiogram demonstrating the effect of Alu I Fragments on the Phosphorylation of PKR. The gel was loaded with hybridization reactions containing purified R-RNA transcript and 10-fold molar excess of Alu I cDNA fragments. Additions of the different Alu I fragments are indicated by a "+". As controls for PKR, one assay contained no added RNA (lane 1) while another assay was supplemented with poly(I)-poly(C) (150 ng/ml) (lane 2) in the kinase reaction. The migration position and molecular weights (×10³) of protein standards, phosphorylase (94 KDa), bovine serum albumin (67 KDa), ovalbumin (45 KDa) and carbonic anhydrase (30 KDa) are indicated on left. Arrow on right indicates the position of PKR.

The purity of the individual fragments is shown in FIG. 11B. Each cDNA fragment was hybridized to the R-RNA transcript individually or in combination. For RNA/DNA hybridization assays (10 µl) reactions contained 100 mM KCl, 0.1 mM EDTA (pH 7.0), R-RNA transcript (5 ng) or poly(I)-poly(C)(3 ng), and were supplemented with a 10-fold molar excess of Alu I DNA fragments or 50–100 ng of complementary oligo as indicated in FIGS. 11C, 12B, and 12C. RNase/DNase-free non-specific *E.coli* DNA was added to reactions as a carrier to minimize loss of RNA transcript during hybridization. Hybridization reactions were for 5 minutes at 95° in tightly capped tubes. The mixtures were allowed to slow cool (30–60 min) to room temperature. Reactions were placed on ice and used directly for protein kinase assays. Controls included parallel hybridization reactions containing: hybridization buffer alone; Alu I fragments alone; oligos alone; poly(I)-poly(C) alone: poly(I)-poly(C) with excess Alu I fragments; and poly(I)-poly(C) with oligos (100 ng) as indicated in FIGS. 11C, 12B, and 12C. All control reactions contained carrier DNA.

Figure 11D:
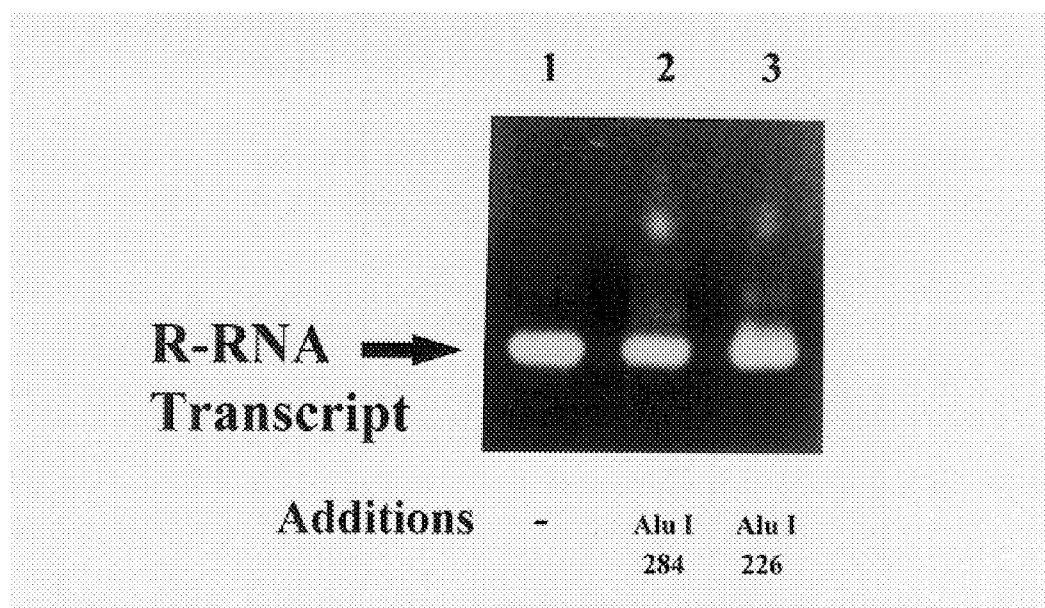
FIG. 11D is a photograph of an ethidium bromide stained agarose gel through which were electrophoresed reactions containing gel purified R-RNA transcript incubated in the presence of 10-fold molar excess of Alu I-284 fragment (lane 2) and Alu I-226 fragment (lane 3). One assay contained only R-RNA transcript (lane 1).

The effect of hybridization of activation of PKR was analyzed utilizing protein kinase assays as described in Example 9. It was determined that the 226 bp fragment alone could prevent the R-RNA transcript from activating PKR (FIG. 11C, compare lanes 3 and 5). The 284, 178 and 133 bp fragments had little or no effect on the R-RNA activity (FIG. 11C, lanes 4,6 and 7). Moreover, in mixing experiments containing all possible combinations of the Alu I fragments, PKR activation was prevented in only those assays which contained the 226 bp fragment (FIG. 11C, lanes 8–14). No phosphorylation of PKR was observed in the absence of ds-RNA (FIG. 11C, lane 1). Controls for hybridization/kinase assays included reactions which contained only poly (I)-poly(C)(FIG.11C, lane 2), and the R-RNA transcript (FIG. 11C, lane 3). The phosphoprotein observed on autoradiograms of lower molecular weight than PKR represent trace amounts of contaminating proteins that vary in PKR preparations. Their phosphorylation is not dependent on RNA and is not affected by the Alu I fragments. The effect of the 226 bp fragments was specific because activation of PKR by poly(I)-poly(C) was not affected by addition of the 226 pb fragments to hybridization reactions and the 226 did not effect the phosphorylation of PKR by the R-RNA without being subjected to hybridization conditions. Moreover, no measurable ribonuclease activity was detected in the 226 pb Alu I fragment to account for loss of RNA (FIG. 11D, lane 3) during hybridization. As an additional control, the 284 bp Alu I fragment was also examined and found to contain no ribonuclease activity (FIG. 11D, lane 2). The 26 bp fragment could not be recovered from gels and directly tested in hybridization reactions. However, in reactions where limited digestion of the 847 bp R-RNA cDNA with Alu I was carried out, a 252 bp fragment identified by additional restriction mapping with Xho I(IBI) as consisting of the 226+26 bp (FIG. 3A) fragment was obtained and purified. The 252 bp fragment was equally effective in preventing PKR activation as the 226 bp fragment following hybridization of the R-RNA (data not shown). These findings indicate that the secondary structures(s) important for the activation of PKR are localized to the 226/252 nt region within the R-RNA transcript consisting of nucleotides 178–430.

EXAMPLE 11

EFFECT OF ANTISENSE OLIGODEOXYNUCLEOTIDES ON THE ACTIVITY OF THE R-RNA

In order to further define the region(s) within the 252 nt fragment of the R-RNA involved in activation of PKR, a novel antisense approach was developed. Eleven short phosphorothioate oligodeoxynucleotides (20–22 nt in length), the sum of which are complementary to the 252 nt stretch of the R-RNA were synthesized. The oligonuolestides were selected for optimal hybridization, and minimal self-folding and homo-dimer annealing. The sequence and size of the oligos used were:

```
OL1A 5'-CTCATCTAGCTTATCCATT-3'      20 mer (SEQ ID NO:6)

OL2A 5'-ATCCGGTTCATACGCCTCATC-3'    21 mer (SEQ ID NO:7)

OL-1 5'-CCTGCAATGATTCCAATTCC-3'     20 mer (SEQ ID NO:8)

OL3A 5'-ATTTAATTCAATAGATGCATAT-3'   22 mer (SEQ ID NO:9)

OL-2 5'TATTGGACGAATGCATTTTG-3'      20 mer (SEQ ID NO:10)

OL4A 5'-TCTTCCTTTGATAGCGACCT-3'     20 mer (SEQ ID NO:11)

OL-3 5'-GAGTAATCAGGATCTTCCTT-3'     20 mer (SEQ ID NO:12)

OL5A 5'-CCTTATGACTTGACCCTCTATA-3'   22 mer (SEQ ID NO:13)

OL-4 5'AGGAGTTGTGCCCAGTCCCA-3'      20 mer (SEQ ID NO:14)

OL6A 5'-TTCATTCTTTTAGCTGACAGC-3'    21 mer (SEQ ID NO:15)

OL7A 5'-CTCAATATCTAGCTTAAATG-3'     20 mer (SEQ ID NO:16)

OLRS 5'-GTTTTACGTAAGCAGGTTAT-3'     20 mer (SEQ ID NO:17)

OLRD 5'-AATGTGTAGTTTCGTACTGA-3'     20 mer (SEQ ID NO:18)
```

Figure 12A:
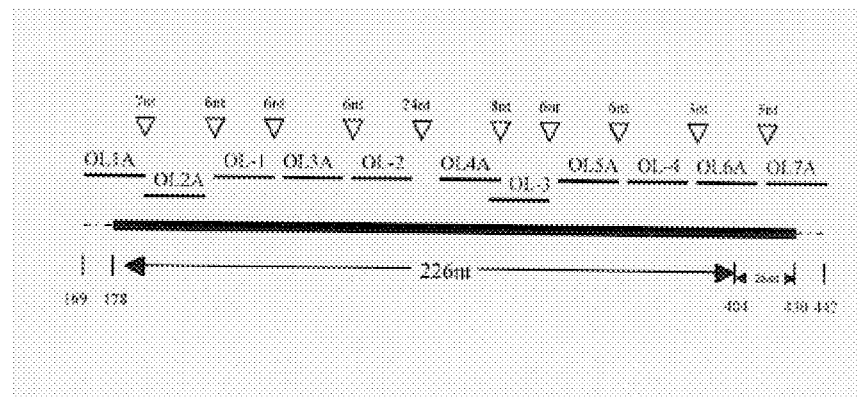
FIG. 12A is a schematic diagram indicating the location and spatial distribution of 11 oligomers complementary to the 252 nt region of the R-RNA. Also indicated are the gaps and overlaps in nucleotides between oligos. The numbers in the lower portion of the figure represent the position of the 226 activation sequence within the R-RNA cDNA sequence.
Figure 12B:
FIG. 12B is an autoradiogram which demonstrates the effect of the subject oligomers on the phosphorylation of PKR. Hybridization reactions and protein kinase assays were carried out as described in Example 10 for FIG. 11C, except that oligomers (50 ng) were added to hybridization reactions as indicated. Controls included hybridization reactions containing: no added RNA (lane 1), poly(I)-poly(C) (lane 2), and R-RNA transcript alone (lane 3).
Figure 12C:
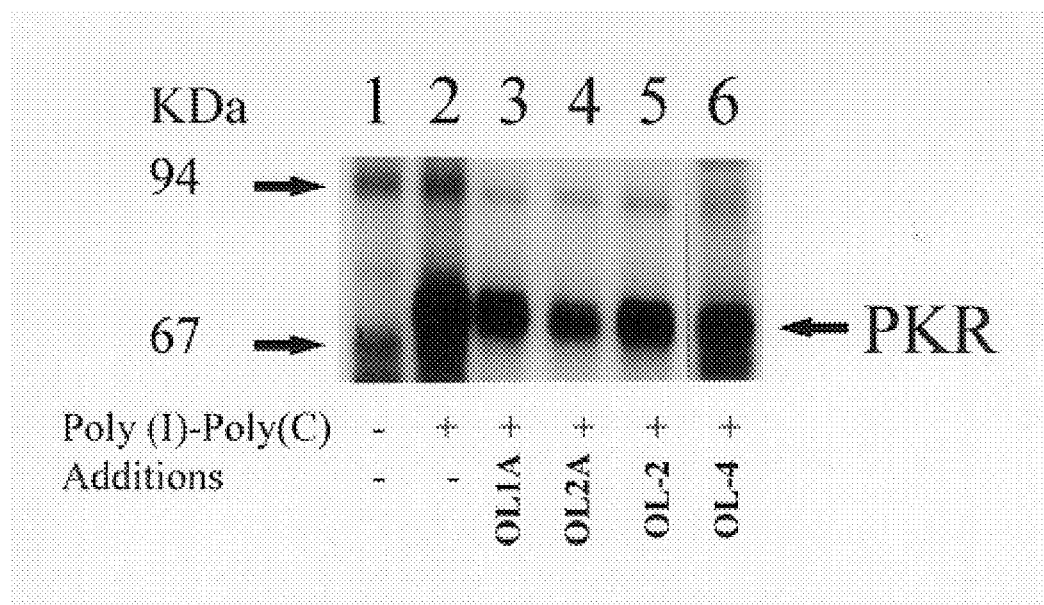
FIG. 12C is an autoradiogram depicting the effect of the subject oligomers on the phosphorylation of PKR by Poly (I)-Poly (C). Hybridization reactions and protein kinase assays were carried out as described in Example 10 for FIG. 3C except poly (I)-poly(C) (150 ng/ml) and oligomers (100 ng) were added to reactions as shown. One hybridization contained no added RNA.
Figure 13:
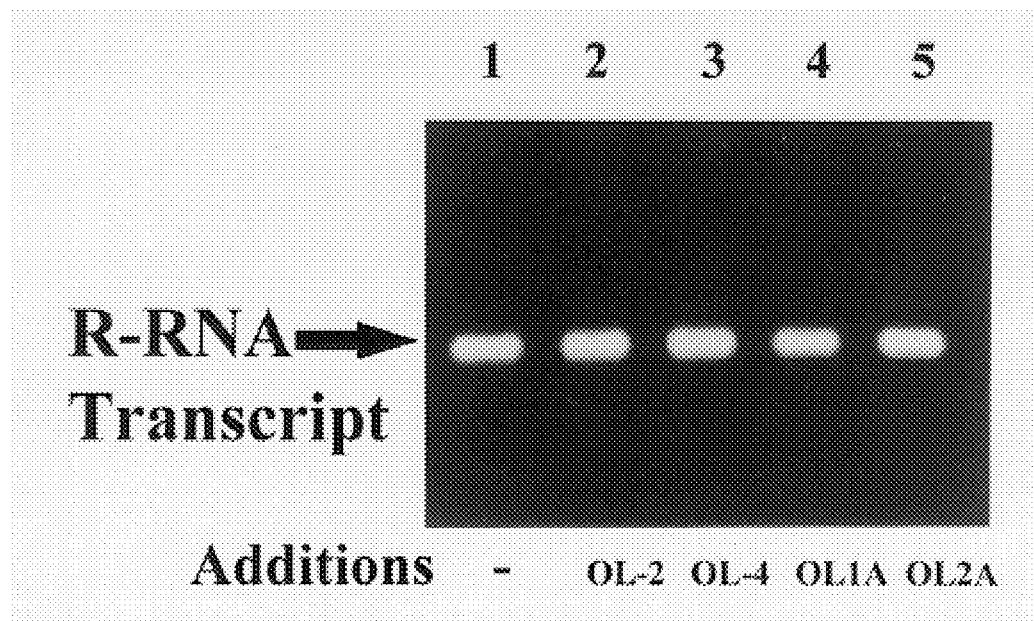
FIG. 13 is a photograph of an ethidium bromide stained agarose gel through which was electrophoresed reactions containing the gel purified R-RNA transcript incubated in the presence of the indicated complementary oligomer (200 ng). Stability of the R-RNA was not effected by the oligomers.

FIG. 12A depicts the location and spatial arrangement of the oligos in respect to the R-RNA. The effect of hybridization of each of these oligos to the R-RNA on the activation of PKR was examined using protein kinase assays. The results indicate that oligos OL1A (SEQ ID NO:6)(FIG. 12B, lane 4), OL2A (SEQ ID NO:7) (FIG. 12, lane 5), OL-2 (SEQ ID NO:10)(FIG. 12B, lane 8) and OL-4 (SEQ ID NO:14) (FIG. 12B, lane 12) were effective in blocking the activation of PKR. The remaining seven oligos had a modest and variable inhibitory effect at identical concentrations, which may be due to nonspecific inhibition because a similar level of reduction was observed with non-complementary oligos (OLRS [SEQ ID NO:17] and OLRD [SEQ ID NO:18]). The largest gap between oligos was 23 nt (between OL-2 [SEQ ID NO:10] and OL4A[SEQ ID NO:11 ]), which alone is insufficient in length for activation of PKR (Manche, et al. 1992, Mol. cell. Biol. 12: 5238–5248). The possibility however, that nucleotides in the gap sequence contributed to other sequences in the 226/252 region for activation of PKR cannot be absolutely excluded. PKR was not phosphorylated in the absence of RNA (FIG. 12B, lane 1). Controls included one assay which contained only poly(I)-poly(C)(FIG. 12B, lane 2) and one assay which contained only R-RNA transcript (FIG. 12B, lane 3). The effects of these blocking oligos appears specific because they had no effect on activation by poly(I)-poly(C)(FIG. 12C, compare lane 2 and lanes 3–6). Moreover, no ribonuclease activity could be detected in blocking oligo preparations, or loss of R-RNA due to addition of these oligos (FIG. 13 compare lane 1 and lanes 2–5). These findings suggest nucleotide sequences 178–202, 263–283 and 374–393 within the R-RNA transcript are involved in the activation of PKR which can be prevented by hybridization to corresponding complementary oligos.

EXAMPLE 12

EFFECT OF OL-2 ON MURINE EMBRYONIC 3T3-F442A FIBROBLASTS

The effect of OL-2 (SEQ ID NO:10) was tested on a variety of cell types and heterogenous cell populations for effects on proliferation, differentiation, and viability. Pre-confluent (log-phase of growth), 3T3-F442A cells cultured under normal conditions and media (10% FBS/DMEM) were treated separately with OL-2 (SEQ ID NO:10) and 2 distinct control oligos. The control oligonucleotides consisted of OLRD (SEQ ID NO:18) and an oligonucleotide having the sequence:

5° CCTCGGTCCCCCCTCGTCCC 3' (SEQ ID NO:19).

Figure 14:
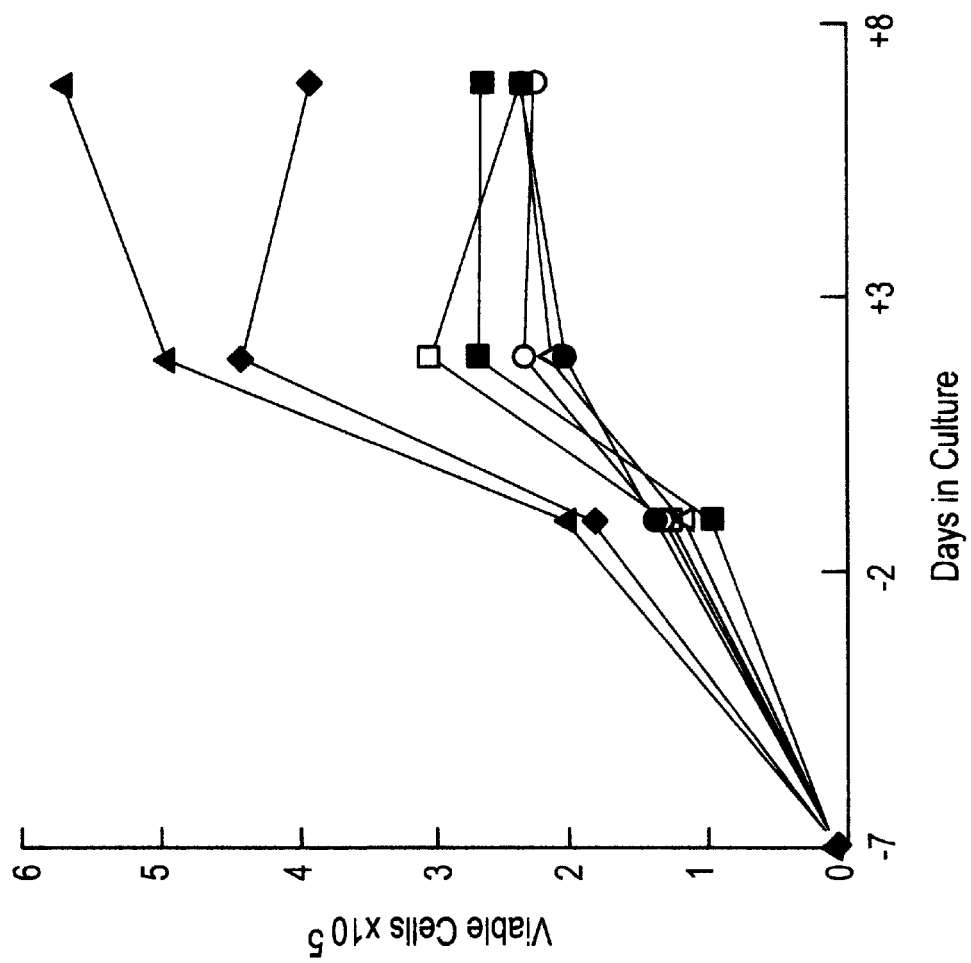
FIG. 14 graphically depicts the effect of antisense oligomers OL-1, OL-2, OL-3, and OL-4 on cell growth. ODN refers to oligodeoxynucleotide (the antisense oligomers) which were added on day 6. Values at each time point are the average of two independent experiments each determined in duplicate. Solid circles represent medium alone; open circles represent an unrelated oligonucleotide; open triangles represent OL-1; solid triangles represent OL-2; open squares represent OL-3; solid squares represent OL-4; solid diamonds represent a mixture of an equal amount of each of OL-1, OL-2, OL-3, and OL-4.

OL-2 (SEQ ID NO:10) was added directly to a cell culture of 3T3-F442A cells to achieve a final concentration of 1.0–10 uM. After three days and again after five days in culture , cells were examined by microscopy and cell numbers were determined by counting using a hemocytometer. As depicted in FIG. 14, it was observed that OL-2 (SEQ ID NO:10) stimulated a 2–3 fold increase in cell number compared to controls resulting in a corresponding increase in saturation density. This increase in saturation density was observed at least between 1.0–10 $\mu$M concentrations of OL-2 (SEQ ID NO:10) and was concentration dependent. No toxicity was observed in cells treated with up to 10 $\mu$M final concentration.

Cell uptake analysis, performed by the method described in Crooke et al. 1995, J. Pharm. Exp. Ther. 275:462–473, indicated that radio-labeled OL-2 (SEQ ID NO:10) was stable and intact intracellularly for up to 72 hours. These results indicate that OL-2 (SEQ ID NO:10) specifically stimulates an increase in cell density as a result of continued cell proliferation in embryonic cells.

EXAMPLE 13

EFFECT OF OL-2 ON HUMAN PERIPHERAL BLOOD MONONUCLEAR CELLS

Fresh drawn human peripheral blood was layered onto Ficoll-Hypague gradients and centrifuged. Unfractioned mononuclear cells were collected and treated with antisense OL-2 (SEQ ID NO:10) and control oligos at final concentrations of 0.5–5 uM. Cells were exposed to the oligos for three days in suspension medium containing Iscoves Modified Eagle's Medium (IMDM) and low serum level, under normal culture conditions. The oligo-treated and control cells were cultured on methylcellulose plates containing erythropoietin, or GM-CSF. Burst-forming units of erythroid lineage (BFU-E) or colony-forming units of granulocyte/macrophage lineage (CFU-GM) were determined by microscopic examination following ten days and 18 days of culture in methylcellulose.

Figure 15:
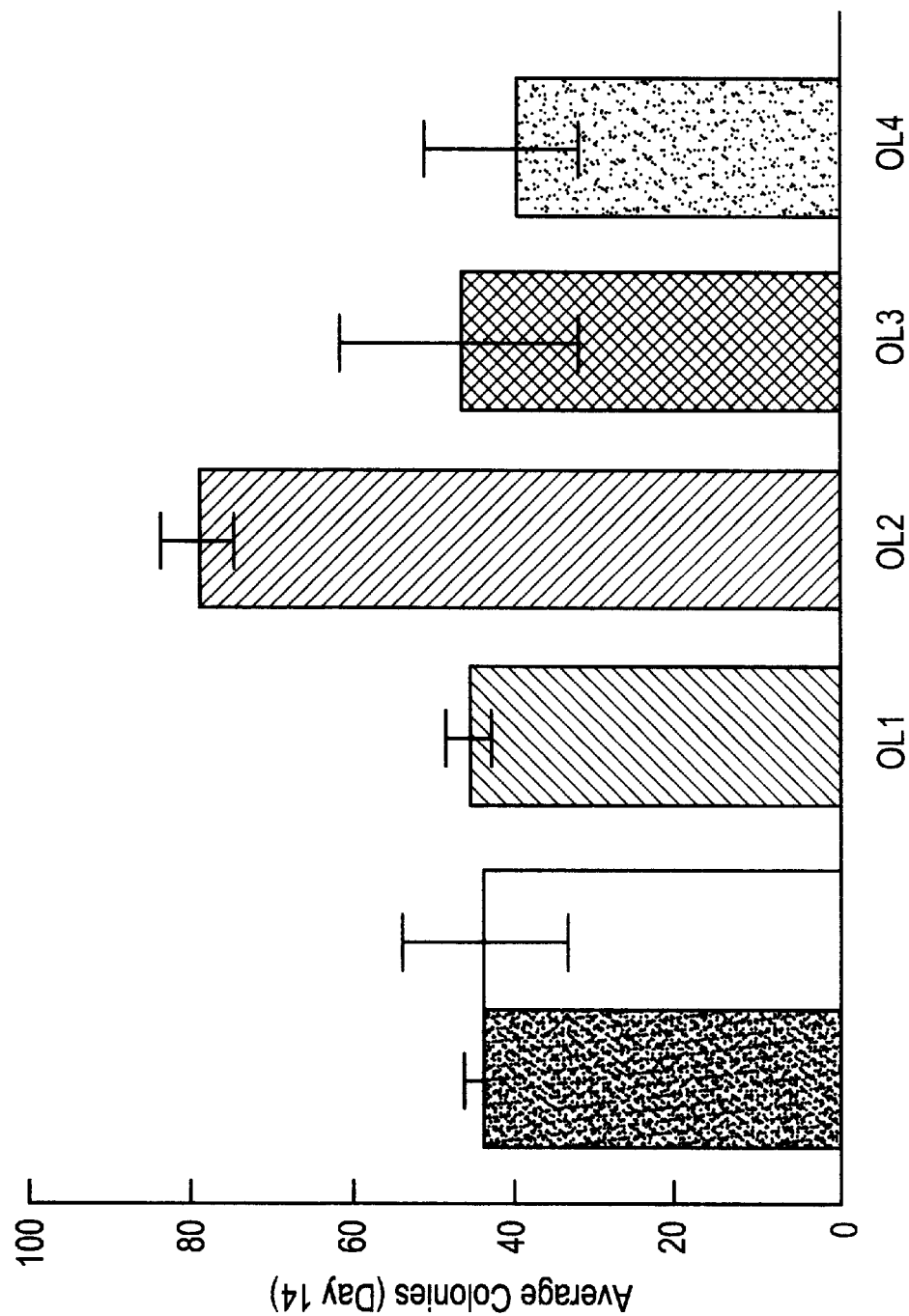
FIG. 15 graphically depicts the effects of OL-1, OL-2, OL-3, and OL-4 on the expansion of burst forming units of erythroid lineage (BFU-E). Human peripheral blood mononuclear cells were treated with 1 µM of oligomers OL-1, OL-2, OL-3, and OL-4. Solid bar represents cells in medium alone, open bar represents treatment with unrelated oligomer.
Figure 16:
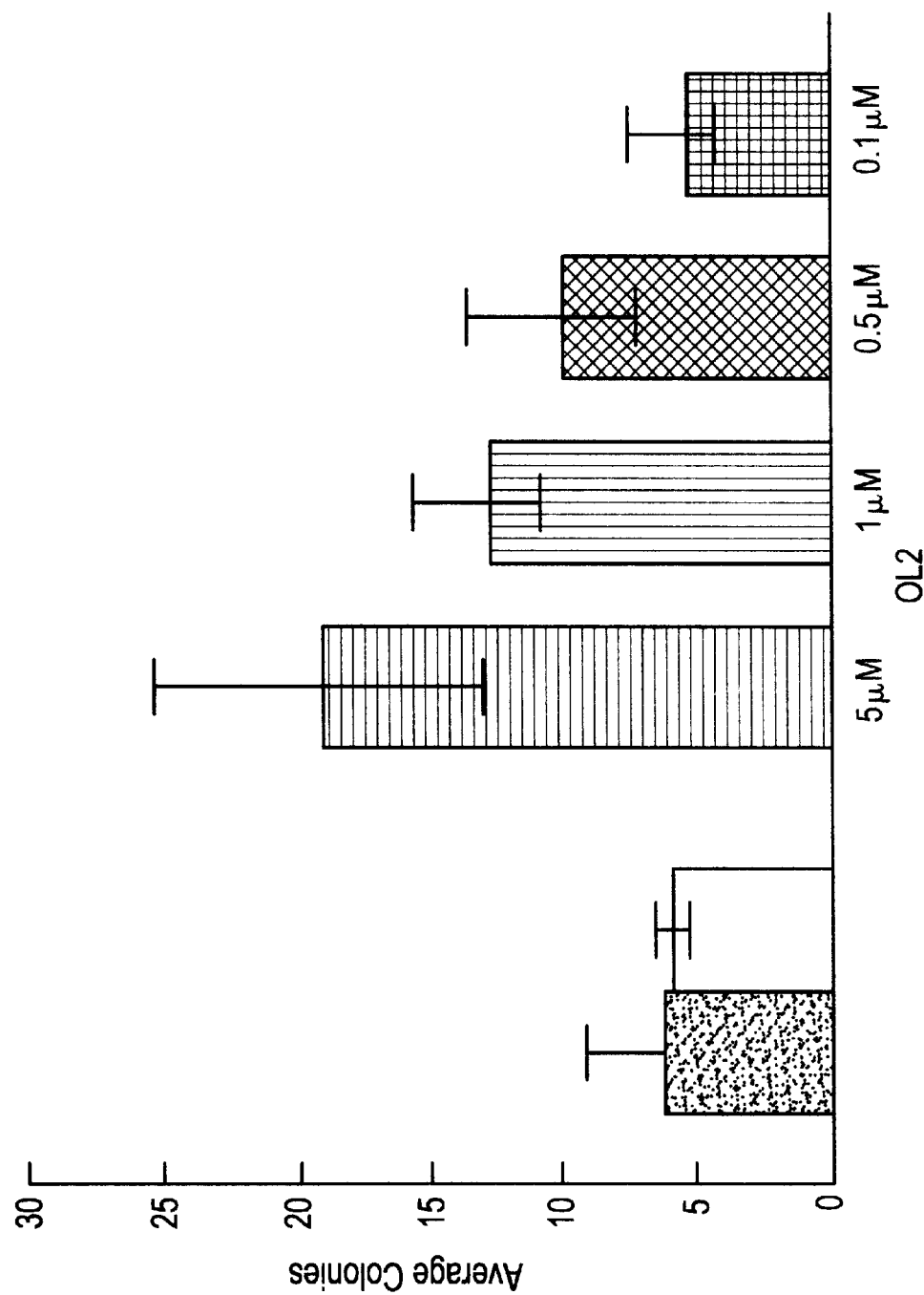
FIG. 16 graphically depicts the effect of OL-2 on expansion of BFU-E at the different concentrations indicated.
Figure 17:
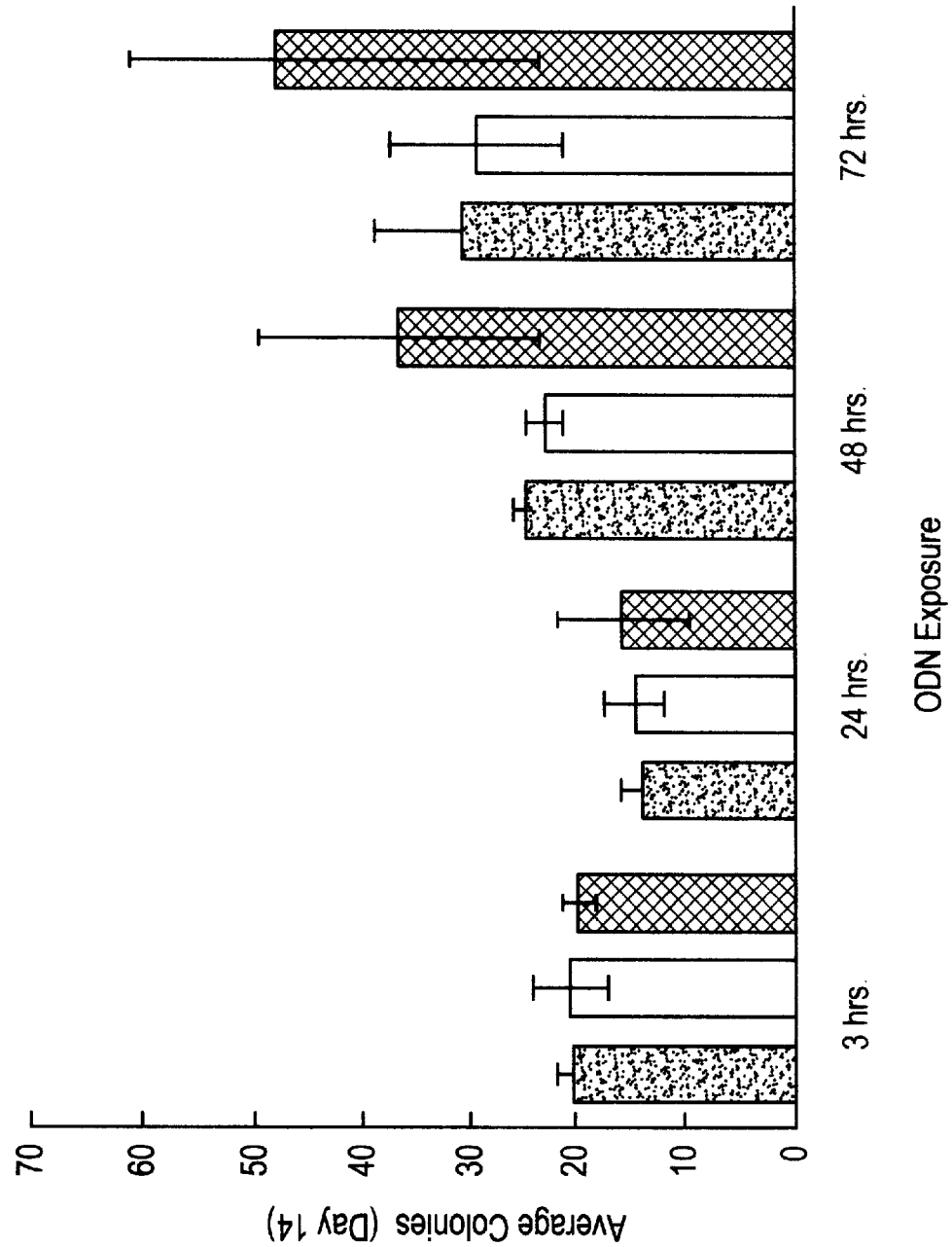
FIG. 17 graphically depicts the effect of OL-2 at a concentration of 1 µM on expansion of BFU-E at the different time points indicated.

FIGS. 15 through 17 illustrate the effect of OL-2 (SEQ ID NO:10) on erythroid progenitors derived from peripheral blood mononuclear cells (PBMC). Controls include medium alone (no oligonucleotides) and an unrelated oligonucleotide having the sequence set forth in SEQ ID NO:19.

FIG. 15 is a graph which depicts results of a representative experiment summarizing the response of four PBMC samples drawn from three individuals. PMBC's were incubated with the oligonucleotides for three days, then analzed for burst forming units—erythroid (BFU-E's), the most primitive erythroid progenitors than can be currently analyzed. Results are expressed as the number of bursts counted per plate (average of triplicate plates). The data indicate that one of the oligonucleotides, OL-2 (SEQ ID NO:10), promotes an approximate 2× increase in burst numbers at a concentration of 1 uM. In addition, cells treated with OL-2 (SEQ ID NO:10) formed larger colonies, indicating the presence of greater cell numbers per colony.

FIG. 16 is a graph which depicts results from an identical assay and demonstrates a dose-dependent increase in burst number. Effects are seen with doses as low as 0.5 uM (1–5× increase). At a dose of 5 $\mu$M (the highest tested), OL-2 (SEQ ID NO:10) exhibited approximately a 4×increase in burst number. No effect was observed in cells treated with the other oligonucleotides (OL-1, OL-2, or OL-4)or a control oligonucleotides having the sequence set forth in SEQ ID NO:19, even at a dose of 5 $\mu$M.

As depicted in FIG. 17, significant increases in BFU-E's (1.5×) were observed between 24 to 48 hours after addition of OL-2 at 1 $\mu$m. Increases (2.5×) were also observed up to 72 hours, the longest time point examined. These results indicate that a time period of between 24–48 hours is sufficient to accumulate an effective intracellular level of OL-2(SEQ ID NO:10).

Thus, OL-2 (SEQ ID NO:10), significantly and specifically promotes an increase in BFU-E numbers. These results indicate that OL-2 (SEQ ID NO:10) selectively increases the population of early progenitor cells (hematopoietic stem cells).

EXAMPLE 14

EFFECT OF OL-2 ON PRIMARY HUMAN MARROW CELLS

Frozen SBA negative (T and B cell depleted) human bone narrow cells (1×10$^7$ cell/vial) were thawed and washed with 2% FBS in IMDM. Cells were resuspended at 1×10$^6$ cells per ml in long term culture-initiating cell medium (LTC-IC) consisting of 12.5% fetal bovine serum (FBS), 12.5% horse serum, 10$^{-6}$M hydrocortisone in IMDM medium. Cells were plated in 48-well plates at 0.5 ml/well to give a cell concentration of 5×10$^5$ cells/well. OL-2 and control oligos were added to achieve a final concentration of 5 $\mu$M/well. Triplicate samples were used for each condition. Oligos were replaced 2-times weekly for three weeks.

After three weeks, cultures were harvested by treatment with collagenase and resuspended in LT-IC medium and re-plated on methylcellulose plates at 4×10$^4$ cells/well. After 3–4 weeks of culture, BFU-Es, CFU-GMs, CFU-GEMM and total CFUs were determined following microscopic examination. Table 1 summarizes the data for one LTC-IC assay. It is concluded that OL-2 (SEQ ID NO:10) and OL-1 (SEQ ID NO:8)alter the cellularity of primary human bone marrow cells. Burst-forming units-erythorid (BRU-E); colony-forming units-granulocyte/macrophage (CFU-CM); colony-forming units-granulocyte/erythroid/myeloid/megakaryocyte (CFU-GEMM) are consistently increased 2.5–7 times with a total cellular increase of approximate 3 fold. No toxicity was observed. The increase in colonies of all major lineages in response to OL-2 (SEQ ID NO:10) and OL-1 (SEQ ID NO:8) indicates an expansion of the pluripotent progenitor cell(s).

TABLE 1

EFFECT OF ANTISENSE OLIGONUCLEOTIDES ON THE CELLULARITY OF HUMAN BONE MARROW

| | BFU-E | CFU-GM | CFU-GEMM | TOTAL CFU |
|---|---|---|---|---|
| control | 1 | 18 | 2 | 21 |
| OL-1 | 7 | 55 | 5 | 67 |
| OL-2 | 7 | 55 | 7 | 69 |

EXAMPLE 15

EFFECT OF OL-2 ON THE CELLULARITY OF MARROW FROM A PATIENT WITH SEVERE CONGENITAL NEUTROPENIA

Fresh marrow was obtained with consent from a patient with Severe Congenital Neutropenia (SCN). Cells were separated by Ficoll-Hypague centrifugation. The buffy coat was collected and resuspended in McCoys media. Cell suspensions (5×10$^5$ cells/ml) were treated with OL-2 (SEQ ID NO:10) (5 $\mu$M), a control oligo, or received no treatment, for 70–245 min. Following this procedure, the cells were plated in methylcellulose LTC-IC media containing granuylocyte/macrophage-colony stimulating factor (GM-CSF) at a concentration of 20–100 ng/ml. Neutrophils were determined after 8–14 days by microscopic inspection and by the specific neutrophil staining for lactoferrin and lactase. It was determined that untreated cells contained no detectable neutrophils. In contrast, marrow treated with OL-2 contained clearly recognizable neutrophils. These results indicate that OL-2 (SEQ ID NO:10) promotes neutrophil expansion and development from a neutrophil depleted SCN marrow. This finding also indicates a clinical benefit for OL-2 (SEQ ID NO:10) in treatment of SCN.

What is claimed is:

1. An isolated antisense molecule consisting of 19 to 252 nucleotides targeted to the nucleotide sequence set forth in SEQ ID NO:1.

2. An isolated antisense molecule consisting of 19 to 252 nucleotides targeted to the nucleotide sequence set forth in SEQ ID NO:2.

3. An isolated antisense molecule targeted to nucleotides 178–430 of SEQ ID NO:1.

4. An isolated nucleic acid molecule consisting of 19–252 nucleotides which hybridizes to nucleotides 178–430 of SEQ ID NO:2 under medium to high stringency conditions wherein said medium stringency conditions comprise about 1–4×SSC, 0.5%–1% SDS(w/v) SDS at greater than or equal to about 45° C. for 2–3 hours and wherein said high stringency conditions comprise about 0.1–1×SSC, 0.1–1% SDS at greater than or equal to about 60° C. for 1–3 hours.

5. An isolated antisense molecule targeted to nucleotides 263–283 of SEQ ID NOs:1 or 2.

6. An isolated nucleic acid molecule consisting of 19–252 nucleotides which hybridizes to nucleotides 263–283 of SEQ ID NO:2 under medium to high stringency conditions wherein said medium stringency conditions comprise about 1–4×SSC, 0.5%–1% SDS(w/v) SDS at greater than or equal to about 45° C. for 2–3 hours and wherein said high stringency conditions comprise about 0.1–1×SSC, 0.1–1% SDS at greater than or equal to about 60° C. for 1–3 hours.

7. An isolated antisense molecule targeted to nucleotides 374–393 of SEQ ID NOs:1 or 2.

8. An isolated nucleic acid molecule consisting of 19–252 nucleotides which hybridizes to nucleotides 374–393 of SEQ ID NO:2 under medium to high stringency conditions wherein said medium stringency conditions comprise about 1–4×SSC, 0.5%–1% SDS(w/v) SDS at greater than or equal to about 45° C. for 2–3 hours and wherein said high stringency conditions comprise about 0.1–1×SSC, 0.1–1% SDS at greater than or equal to about 60° C. for 1–3 hours.

9. An oligonucleotide comprising the sequence set forth in SEQ ID No. 6.

10. An oligonucleotide comprising at least eight contiguous nucleotides derived from the sequence set forth in SEQ ID NO:6.

11. An oligonucleotide comprising the sequence set forth in SEQ ID No. 7.

12. An oligonucleotide comprising at least eight contiguous nucleotides derived from the sequence set forth in SEQ ID NO:7.

13. An oligonucleotide comprising the sequence set forth in SEQ ID No. 10.

14. An oligonucleotide comprising at least eight contiguous nucleotides derived from the sequence set forth in SEQ ID NO:10.

15. An oligonucleotide comprising the sequence set forth in SEQ ID No.14.

16. An oligonucleotide comprising at least eight contiguous nucleotides derived from the sequence set forth in SEQ ID NO:14.

17. An antisense oligonucleotide comprising at least eight nucleotides targeted to nucleotides 178–430 of SEQ ID NO:1.

18. A method of stimulating cell proliferation in a cell culture which comprises contacting said cell culture with an effective amount of an oligonucleotide comprising the sequence set forth in SEQ ID NO:10 or at least eight contiguous nucleotides of SEQ ID NO:10.

19. A method of inhibiting the activation of PKR in a cell culture which comprises contacting said cell culture with an effective amount of at least one of an isolated antisense molecule targeted to SEQ ID NO:1, an isolated antisense molecule targeted to nucleotides 178–430 of SEQ ID NOs:1 or 2, an isolated antisense molecule targeted to nucleotides 263–283 of SEQ ID NOs:1 or 2, an isolated antisense molecule targeted to nucleotides 374–393 of SEQ ID NOs:1 or 2; an oligonucleotide having the sequence set forth in SEQ ID NO:6 or at least eight contiguous nucleotides of SEQ ID NO:6, an oligonucleotide having the sequence set forth in SEQ ID NO:7 or at least eight contiguous nucleotides of SEQ ID NO:7, an oligonucleotide having the sequence set forth in SEQ ID NO:10 or at least eight contiguous nucleotides of SEQ ID NO:10, or an oligonucleotide having the sequence set forth in SEQ ID NO:14 or at least eight contiguous nucleotides of SEQ ID NO:14.

20. A method of inhibiting cell proliferation in bone marrow cells obtained from a patient suffering from a hematological cancer which comprises isolating a bone marrow sample from a patient suffering from a hematological cancer, contacting the cells in said sample with an effective amount of at least one of an R-RNA having the sequence set forth in SEQ ID NO:2, a portion of an R-RNA having nucleotides 178–430 of SEQ ID NO:2, a portion of an R-RNA having nucleotides 263–283 of SEQ ID NO:2, or a portion of an R-RNA having nucleotides 374–393 of SEQ ID NO:2, and after a sufficient time, transplanting said cells back into the donor patient.

21. A method for promoting expansion of pluripotent progenitor cells which comprises obtaining bone marrow cells from a patient and contacting said cells with an effective amount of an oligonucleotide selected from the group consisting of an oligonucleotide having the nucleotide sequence set forth in SEQ ID NO:10, an oligonucleotide having at least eight contiguous nucleotides of SEQ ID NO:10, an oligonucleotide having the nucleotide sequence set forth in SEQ ID NO:8, and an oligonucleotide having at least eight contiguous nucleotides of SEQ ID NO:8.

22. A method for promoting expansion of hematopoietic stem cells which comprises obtaining peripheral blood from a patient; isolating mononuclear cells and contacting said mononuclear cells with an effective amount of an oligonucleotide having the nucleotide sequence set forth in SEQ ID NO:10 or at least eight contiguous nucleotides of SEQ ID NO:10.

23. A method for promoting neutrophil expansion and development from a neutrophil depleted marrow cell culture which comprises obtaining marrow cells from a patient suffering from severe congenital neutropenia (SCN), contacting said cells with an effective amount of an oligonucleotide having the sequence set forth in SEQ ID NO:10 or at least eight contiguous nucleotides of SEQ ID NO:10, and after a sufficient time, transplanting the marrow cells back into the patient.

24. A method for expanding hematopoietic cells in umbilical cord blood which comprises contacting a sample of the cord blood with at least one oligonucleotide selected from the group consisting of an oligonucleotide having the sequence set forth in SEQ ID NO:8, an oligonucleotide having at least eight contiguous nucleotides as set forth in SEQ ID NO:8, an oligonucleotide having the sequence set forth in SEQ ID NO:10 or an oligonucleotide having at least eight contiguous nucleotides as set forth in SEQ ID NO:10.

25. A composition comprising a cell culture medium and at least one of a nucleic acid molecule or oligonucleotide admixed with said cell culture medium selected from the group consisting of an isolated antisense molecule targeted to SEQ ID NO:1, an isolated antisense molecule targeted to nucleotides 178–430 of SEQ ID NOS:1 or 2, an isolated antisense molecule targeted to nucleotides 263–283 of SEQ ID NOS:1 or 2, an isolated antisense molecule targeted to nucleotides 374–393 of SEQ ID NOS:1 or 2; an oligonucleotide having the sequence set forth in SEQ ID NO:6 or at least eight contiguous nucleotides of SEQ ID NO:6, an oligonucleotide having the sequence set forth in SEQ ID NO:7 or at least eight contiguous nucleotides of SEQ ID NO:7, an oligonucleotide having the sequence set forth in SEQ ID NO:10 or at least eight contiguous nucleotides of SEQ ID NO:10, or an oligonucleotide having the sequence set forth in SEQ ID NO:14 or at least eight contiguous nucleotides of SEQ ID NO:14.

26. A vector comprising the isolated antisense molecule of any one of claims 1–3, 5, 7, or 17.

27. A vector comprising the isolated nucleic acid molecule of any one of claims 4, 6, or 8.

* * * * *